US010275958B2

(12) United States Patent
Daugbjerg et al.

(10) Patent No.: US 10,275,958 B2
(45) Date of Patent: *Apr. 30, 2019

(54) ENHANCED MODULAR DRAWER STRUCTURES, SYSTEMS, AND METHODS

(71) Applicant: GCX Corporation, Petaluma, CA (US)

(72) Inventors: Cristian J. Daugbjerg, Petaluma, CA (US); Robert Peter Glaser, Corte Madera, CA (US); Carl Hermann Poppe, Danville, CA (US)

(73) Assignee: APPLIED INVENTION, LLC, Burbank, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/153,584

(22) Filed: May 12, 2016

(65) Prior Publication Data

US 2016/0260272 A1  Sep. 8, 2016

Related U.S. Application Data

(63) Continuation of application No. 13/087,176, filed on Apr. 14, 2011, now Pat. No. 9,367,984.

(51) Int. Cl.
*G07C 9/00* (2006.01)
*G06F 19/00* (2018.01)
(Continued)

(52) U.S. Cl.
CPC .......... *G07C 9/00142* (2013.01); *A47B 88/57* (2017.01); *A61G 12/001* (2013.01);
(Continued)

(58) Field of Classification Search
CPC ............ E05B 65/46; A47B 2200/0023; A47B 2210/0018; G07C 9/00142; G07C 9/00158; G06F 19/3462
(Continued)

(56) References Cited

U.S. PATENT DOCUMENTS

| 5,174,223 A | 12/1992 | Nagy et al. |
| 5,518,310 A | 5/1996 | Ellman et al. |

(Continued)

FOREIGN PATENT DOCUMENTS

| JP | H7-225879 | 8/1995 |
| JP | H11503934 | 4/1996 |

(Continued)

*Primary Examiner* — Michael Collins
(74) *Attorney, Agent, or Firm* — Michael A. Glenn; Perkins Coie LLP

(57) ABSTRACT

A modular drawer structure comprises a housing having an interior volume defined therein, and a drawer comprising one or more compartments, wherein the drawer is slidably movable with respect to the interior volume of the housing between a first closed position, wherein the compartments are enclosed within the interior volume, and a second open position, wherein the compartments are at least partially accessible. The drawer structure further comprises a mechanism for controllably locking the drawer in the first closed position, an access pad, e.g. such as but not limited to a keypad and/or a card swipe pad, for entry of a passcode, and a processor for unlocking the drawer when an entered passcode matches a stored passcode value. Some embodiments of the drawer structure include a stored time threshold, wherein if the drawer is unlocked for a time that meets or exceeds the stored time threshold, the drawer is relocked.

20 Claims, 15 Drawing Sheets

(51) Int. Cl.
*A61G 12/00* (2006.01)
*G07G 1/00* (2006.01)
*G07G 3/00* (2006.01)
*E05B 65/46* (2017.01)
*G07F 17/00* (2006.01)
*A47B 88/57* (2017.01)
*E05B 47/00* (2006.01)
*A47B 23/04* (2006.01)
*A47B 31/00* (2006.01)
*A47B 88/90* (2017.01)

(52) U.S. Cl.
CPC .............. *E05B 65/46* (2013.01); *G06F 19/00* (2013.01); *G06F 19/3462* (2013.01); *G07C 9/00158* (2013.01); *G07F 17/0092* (2013.01); *G07G 1/0027* (2013.01); *G07G 3/003* (2013.01); *A47B 23/046* (2013.01); *A47B 88/90* (2017.01); *A47B 2031/006* (2013.01); *A47B 2200/0023* (2013.01); *A47B 2210/0018* (2013.01); *A61G 2205/10* (2013.01); *E05B 47/00* (2013.01)

(58) Field of Classification Search
USPC ...................................... 700/237; 312/249.11
See application file for complete search history.

(56) References Cited

U.S. PATENT DOCUMENTS

| | | | |
|---|---|---|---|
| 5,673,983 A * | 10/1997 | Carlson | A47B 67/04 312/218 |
| 5,745,366 A | 4/1998 | Higham et al. | |
| 5,795,044 A | 8/1998 | Trewhella, Jr. et al. | |
| 6,065,819 A | 5/2000 | Holmes et al. | |
| 6,338,007 B1 | 1/2002 | Broadfield et al. | |
| 6,339,732 B1 | 1/2002 | Phoon et al. | |
| 6,493,220 B1 * | 12/2002 | Clark | A47B 21/00 248/918 |
| 6,902,083 B1 | 6/2005 | Michael et al. | |
| 6,996,455 B2 | 2/2006 | Eggenberger et al. | |
| 7,040,504 B2 | 5/2006 | Broadfield et al. | |
| 7,142,944 B2 | 11/2006 | Holmes et al. | |
| 7,426,425 B2 * | 9/2008 | Meek, Jr. | E05B 47/0002 312/216 |
| 7,668,620 B2 | 2/2010 | Shoenfeld | |
| 7,747,347 B2 | 6/2010 | Park, IV et al. | |
| 7,782,607 B2 | 8/2010 | Harbin et al. | |
| 7,828,253 B2 | 11/2010 | Meyer et al. | |
| 7,952,315 B2 | 5/2011 | Park, IV et al. | |
| 8,019,470 B2 | 9/2011 | Meek, Jr. et al. | |
| 8,109,527 B2 | 2/2012 | Bustle et al. | |
| 8,160,727 B2 | 4/2012 | Coonan et al. | |
| 8,169,191 B2 * | 5/2012 | Werthman | A61B 5/0002 320/107 |
| 8,180,485 B2 | 5/2012 | Reckelhoff et al. | |
| 8,196,939 B2 | 6/2012 | Bustle et al. | |
| 8,197,017 B2 | 6/2012 | Rahilly et al. | |
| 8,412,375 B2 | 4/2013 | Schifman et al. | |
| 8,495,898 B2 | 7/2013 | Gokcebay et al. | |
| 8,554,365 B2 * | 10/2013 | Thomas | G06F 19/3462 700/236 |
| 8,616,136 B2 | 12/2013 | Burgess et al. | |
| 8,814,107 B2 | 8/2014 | Hampe et al. | |
| 9,139,213 B2 | 9/2015 | Trish et al. | |
| 9,367,061 B2 * | 6/2016 | Miller | G05B 19/042 |
| 9,367,984 B2 * | 6/2016 | Daugbjerg | G06F 19/3462 |
| 2002/0165641 A1 | 11/2002 | Manalang et al. | |
| 2004/0262867 A1 * | 12/2004 | Arceta | A61G 12/001 280/47.35 |
| 2006/0125356 A1 | 6/2006 | Meek et al. | |
| 2007/0228680 A1 * | 10/2007 | Reppert | A47B 21/00 280/47.35 |
| 2007/0244598 A1 | 10/2007 | Shoenfeld et al. | |
| 2009/0015116 A1 | 1/2009 | Arceta et al. | |
| 2009/0108016 A1 | 4/2009 | Brown et al. | |
| 2009/0212670 A1 * | 8/2009 | Bustle | A47B 21/0314 312/209 |
| 2009/0276104 A1 | 11/2009 | Coonan et al. | |
| 2010/0004780 A1 | 1/2010 | Rickelhoff et al. | |
| 2010/0106291 A1 | 4/2010 | Campbell et al. | |
| 2010/0213679 A1 * | 8/2010 | Smith | A47B 21/00 280/47.35 |
| 2011/0001407 A1 * | 1/2011 | Stradiota | E05B 65/0075 312/237 |
| 2012/0004764 A1 * | 1/2012 | Rahilly | G06F 19/3462 700/225 |
| 2012/0203377 A1 * | 8/2012 | Paydar | G01K 3/005 700/232 |

FOREIGN PATENT DOCUMENTS

| | | |
|---|---|---|
| JP | H8-226266 | 9/1996 |
| JP | 8-326370 | 12/1996 |
| JP | 2002516228 A | 6/2002 |
| JP | 2005-34607 | 2/2005 |

* cited by examiner

ENHANCED MODULAR DRAWER STRUCTURES, SYSTEMS, AND METHODS

CROSS REFERENCE TO RELATED APPLICATIONS

This application is a continuation of U.S. patent application Ser. No. 13/087,176 filed Apr. 14, 2011, which is incorporated by reference herein in its entirety.

FIELD OF THE INVENTION

The present invention relates to the field of drawer structures. More particularly, the present invention relates to improved modular drawer structures and associated processes that may be implemented for dispensing within a medical environment.

BACKGROUND OF THE INVENTION

Dispensing cabinets, cassettes and trays are often used to for any of storage, transportation, or distribution of medications, such as within a hospital environment. FIG. 1 is a perspective view of a simplified tray 10, such as comprising a tray structure 12, e.g. having an exemplary length 14, width 16, and height 18. The tray 12 has an interior region 20 defined therein, wherein a divider system 22 may be installed or defined therein, such as comprising one or more panels 24 and connectors 25, to create a plurality of storage compartments 26, e.g. 26a-26k, within the interior region 20 of the tray 12.

Automated dispensing cabinets (ADCs) have been used for several years within many hospital settings, for the decentralized storage and distribution of medications. Exemplary ADCs in use at this time are the Pyxis® MedStation®, available through CareFusion Corp., of San Diego, Calif., and PROmanager Rx™, available through McKesson Corp., of San Francisco, Calif.

Other carts and storage cabinets are also available that provide for storage within patient care areas, such as to cut down on trips to an ADC. Such carts and cabinets are required to be replenished by a hospital pharmacy, are inherently limited in their storage capacity, and are often not adequately mobile to move from room to room.

Hospitals commonly purchase medications in bar-coded single dose packages that are stored in ADCs. Computers associated with hospital pharmacies allow review of orders before a drug is administered. ADCs allow authorized access to medication within a patient care area, such as by a nurse or clinician, wherein the ADC dispenses medications to the nurse or caregiver, for subsequent transport and administration to the patient.

Patient-specific trays or cassettes are commonly filled with unit-dose medications, such as at a hospital pharmacy or from an ADC, wherein the cassettes are typically delivered to a nursing unit, where they may be stored within medication cabinets or carts. At the time of administration, the attending doctor, nurse or clinician records the administration of medications in an electronic medical administration record (eMAR).

A significant portion of a nurse's time is associated with the administration of medications, and each patient commonly receives several medications on any given round. While it is often preferred that a nurse transports medications for administration to a single patient at a time, such as due to concerns for safety, this requires a great deal of time and travel for a nurse. Based upon the proximity of the ADC, it is sometimes desired that medications for more than one patient be stored on a cart. While some institutions forbid this, as it increases the risk of administering the wrong medication, other institutions allow the simultaneous storage and transport of medications for multiple patients.

FIG. 2 is a flow chart of an exemplary workflow process cycle 50 for dispensing medications with an automated dispensing cabinet and a conventional dispensing tray or cassette. For example, a pharmacy typically fills or replenishes 52 the automated dispensing cabinet. A nurse then gets 54 the medications from the automated dispensing cabinet and fills a tray or cassette, while checking 56 the medications against order information. The nurse may proceed 58 as needed to get any missing medications, refrigerated medications, and/or solution bags, etc., and then transport 60 the medications to a patient. The nurse then typically bar codes 62 both the patient, e.g. having an identification bracelet, and the medications, such as to provide inventory control and to prevent human errors. The nurse then prepares 64 the medications as necessary, such as but not limited to cutting pills, and/or dissolving medications in water. The nurse then administers 66 the medications, verifies 68 ingestion of the medications, and makes 70 an electronic medication record, such as associated with the patient chart. The nurse then typically discards 72 any wrappers if needed, and disposes 74 of any waste medications, such as with secondary verification.

The simplified tray 10 seen in FIG. 1, such as when placed on a cart for transportation to a patient, does not inherently provide security for the contents that may be carried within, wherein contents may readily fall out, be stolen, and/or tampered with. Such an inherently low level of security at any point during a workflow process, such as seen in FIG. 2, can pose undue risk to the patient or to others. As well, caregivers are frequently interrupted during their process of accessing, transporting, and/or administering medications, and often have to find or locate a second nurse to verify administration, such as for a high-risk drug, thus increasing the risk further.

It would therefore be advantageous to provide a medical drawer structure that provides enhanced security during a workflow process associated with the transport and administration of medications.

Some prior cabinets and carts provide keyless entry for standard drawers, such as with a keypad or electronic key lock assembly. However, such structures typically require the use of simple medical trays, e.g. 10, to be placed within such drawers. Discrete medical trays that are placed within such a lockable drawer are not directly tracked as to their location and access, wherein the drawer is not directly dockable to the drawer or cabinet system. Such a tray may be absent from the drawer when the drawer is in the closed and locked position.

It would therefore be advantageous to provide a medical drawer structure that provides direct docking and security for a dispensing tray. The development of such a structure would constitute a major technological advance.

While some mobile carts include mechanical locks to provide security for medication trays or cassettes, such locks require a mechanical key for operation. However, keys are easily lost, and do not provide any traceability to individual users. While some prior carts have included keyless entry for one or more standard drawers, such drawers are not configured to be removable, and when used for dispensing medications, require a separate tray or cassette to be stored within and removed therefrom, e.g. such as a tray 10 as seen in FIG. 1.

It would therefore be advantageous to provide a removable drawer structure that provides lockable access to medications, without the use of mechanical keys. The development of such a drawer structure would constitute an additional technological advance. As well, it would be advantageous to provide a removable drawer structure that provides traceability to individual users. The development of such a drawer structure would constitute a further technological advance.

While stationary cabinets can provide security for medications, such as for storage at a nurses station, medical dispensing trays and cassettes are commonly required to be transported throughout a medical facility, and are commonly required to be scanned at a location of administration to a patient.

It would therefore be advantageous to provide a secure dispensing drawer structure that is readily integrated into a mobile cart, which can be readily moved throughout a work area. The development of such a drawer structure would constitute a major technological advance. Furthermore, it would be advantageous to provide such a secure mobile drawer structure that is readily integrated with other equipment, such as to provide any of barcode scanning, alarms, and/or patient charting. The development of such a system would constitute a further technological advance.

SUMMARY OF THE INVENTION

A modular drawer structure comprises a drawer housing having an interior volume defined therein, and a drawer comprising one or more compartments, wherein the drawer is slidably movable with respect to the interior volume of the drawer housing between a first closed position, wherein the compartments are securely enclosed within the interior volume, and a second open position, wherein the drawer compartments are at least partially accessible. The drawer structure further comprises a mechanism for controllably locking the drawer in the first closed position, an access pad, e.g. such as but not limited to a keypad and/or a card swipe pad, mounted to the drawer housing for entry of a passcode, and a processor for unlocking the locking mechanism when an entered passcode matches a stored passcode value. Some embodiments of the drawer structure include a stored time threshold, wherein if the drawer unlocked for a time that meets or exceeds the stored time threshold, the drawer returns to a locked position, thus providing security for an unattended drawer, and requiring a user to reenter a passcode to unlock the drawer and gain access to the contents therein.

DETAILED DESCRIPTION OF PREFERRED EMBODIMENTS

Figure 1:
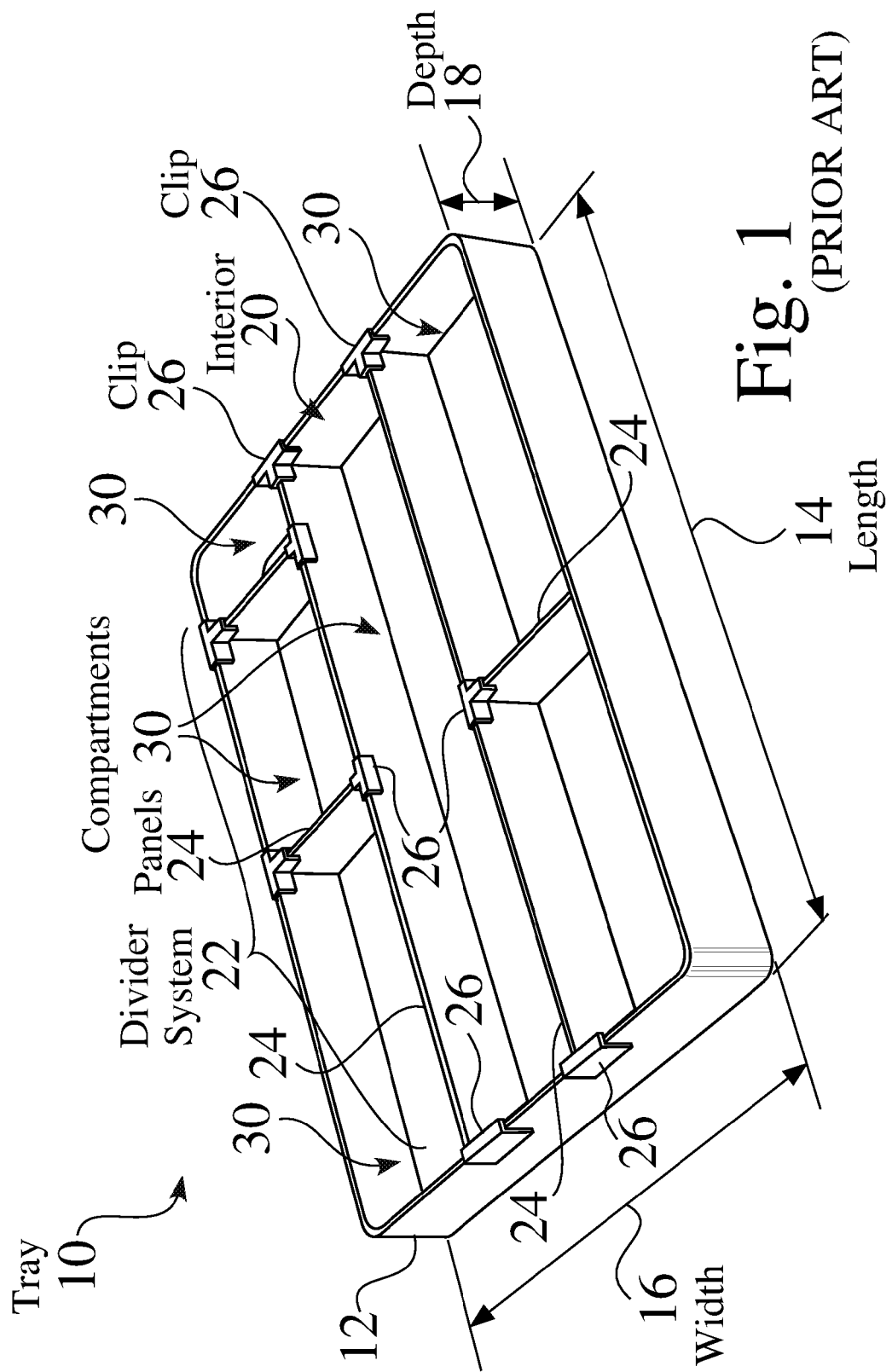
FIG. 1 is a perspective view of an exemplary conventional medical dispensing tray.
Figure 2:
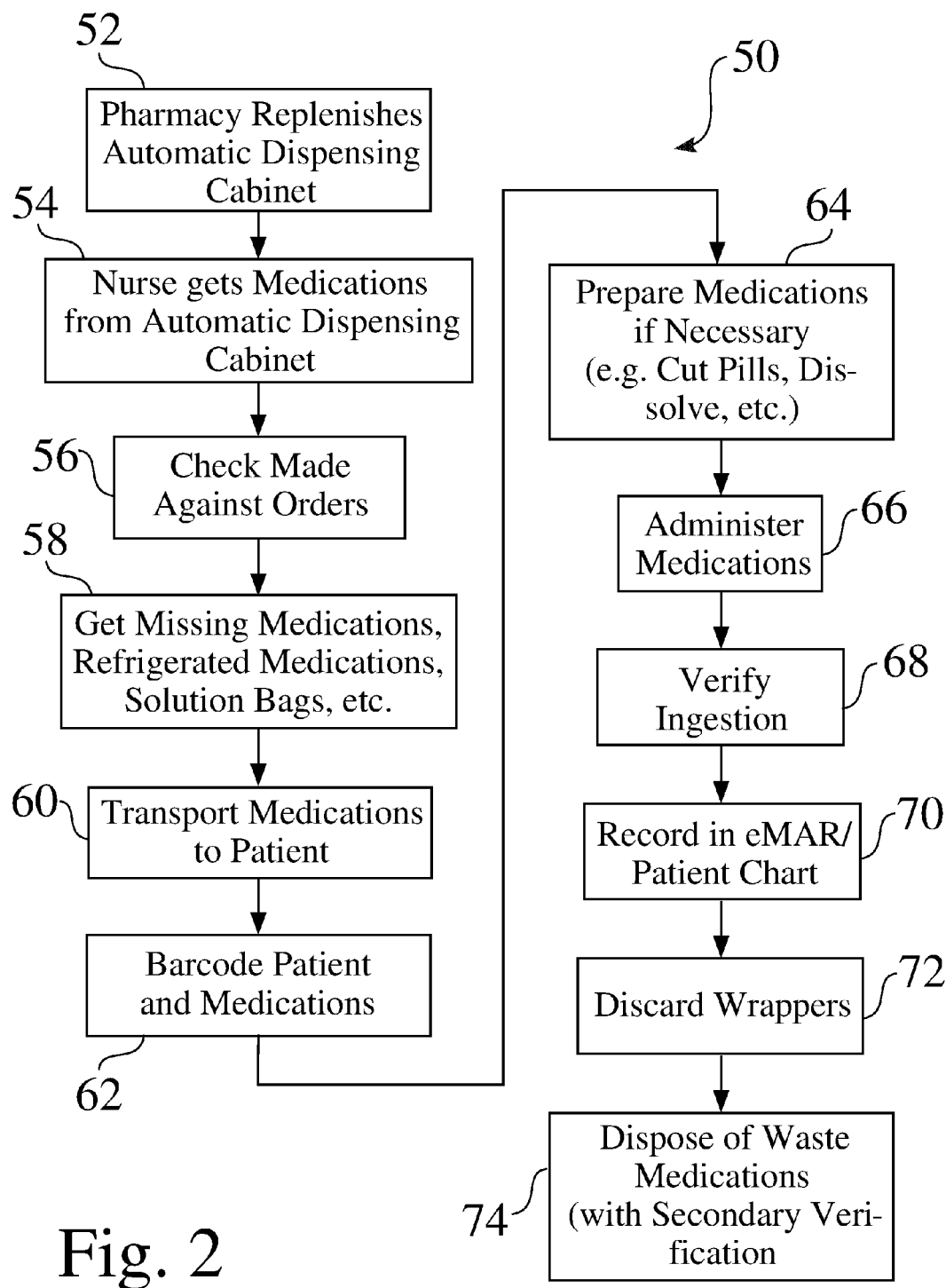
FIG. 2 is a flow chart of an exemplary process for dispensing medications with a conventional tray or cassette.
Figure 3:
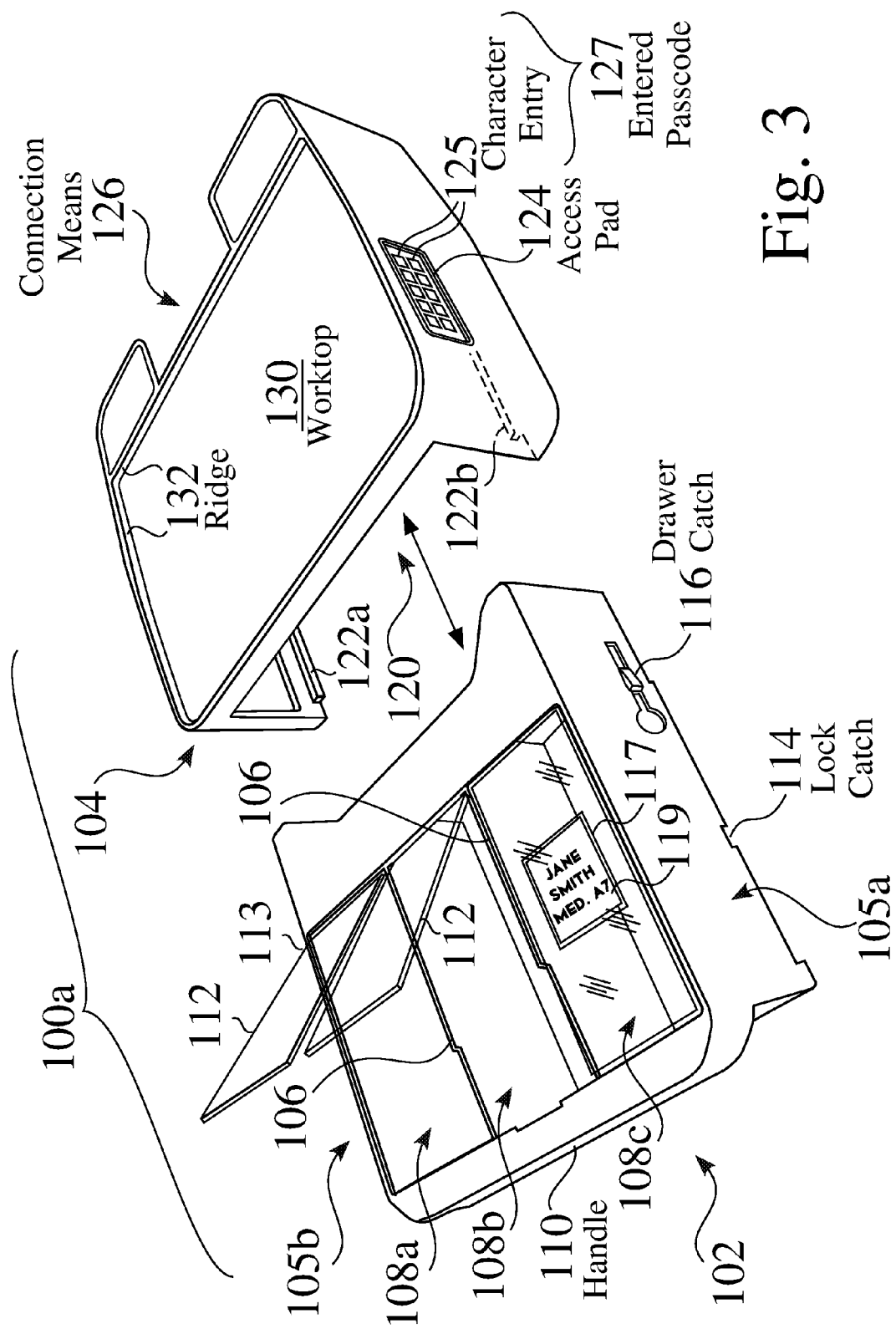
FIG. 3 is an expanded perspective view of an enhanced drawer structure.
Figure 4:
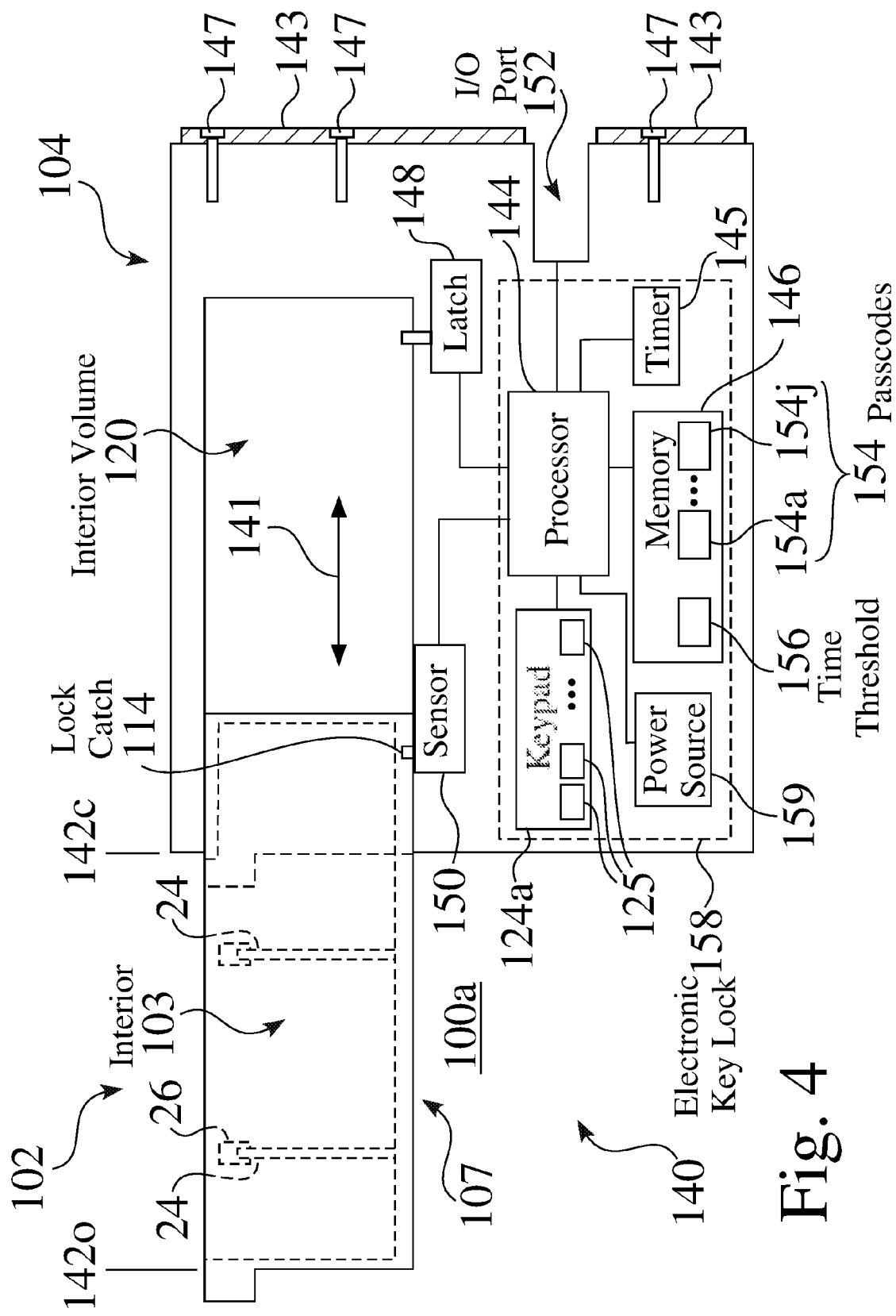
FIG. 4 is s simplified functional schematic view of an enhanced drawer structure.
Figure 16:
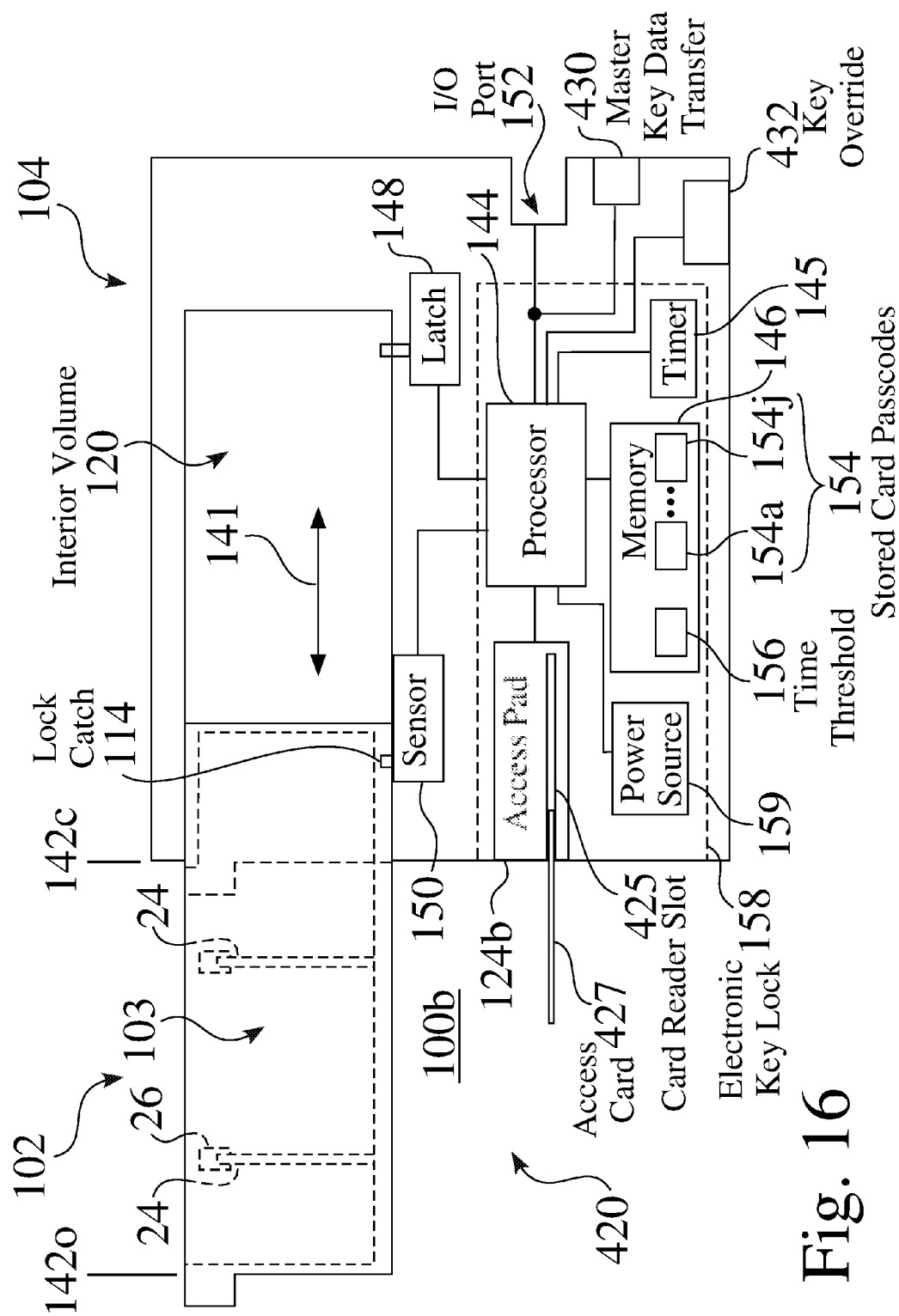
FIG. 16 is a simplified functional schematic view of an alternate enhanced drawer structure.

FIG. 3 is an expanded perspective view of an enhanced drawer structure 100, e.g. 100a. FIG. 4 is a simplified functional schematic view 140 of an enhanced drawer structure 100, e.g. 100a. The enhanced drawer structure 100 comprises at least one drawer 102, which is slidably movable 141 within a drawer housing 104, such as to open 141o (FIG. 13) from a closed position 142c and an open position 142o, and/or to close 141c (FIG. 12) from an open position 142o to a closed position 142c. The enhanced drawer structure 100 further comprises a lock or latch 148, which is controllably activated through an access pad 124, such as a keyless entry module 124, e.g. such as but not limited to any of keypad 124a or a card swipe pad 124b (FIG. 16).

Figure 5:
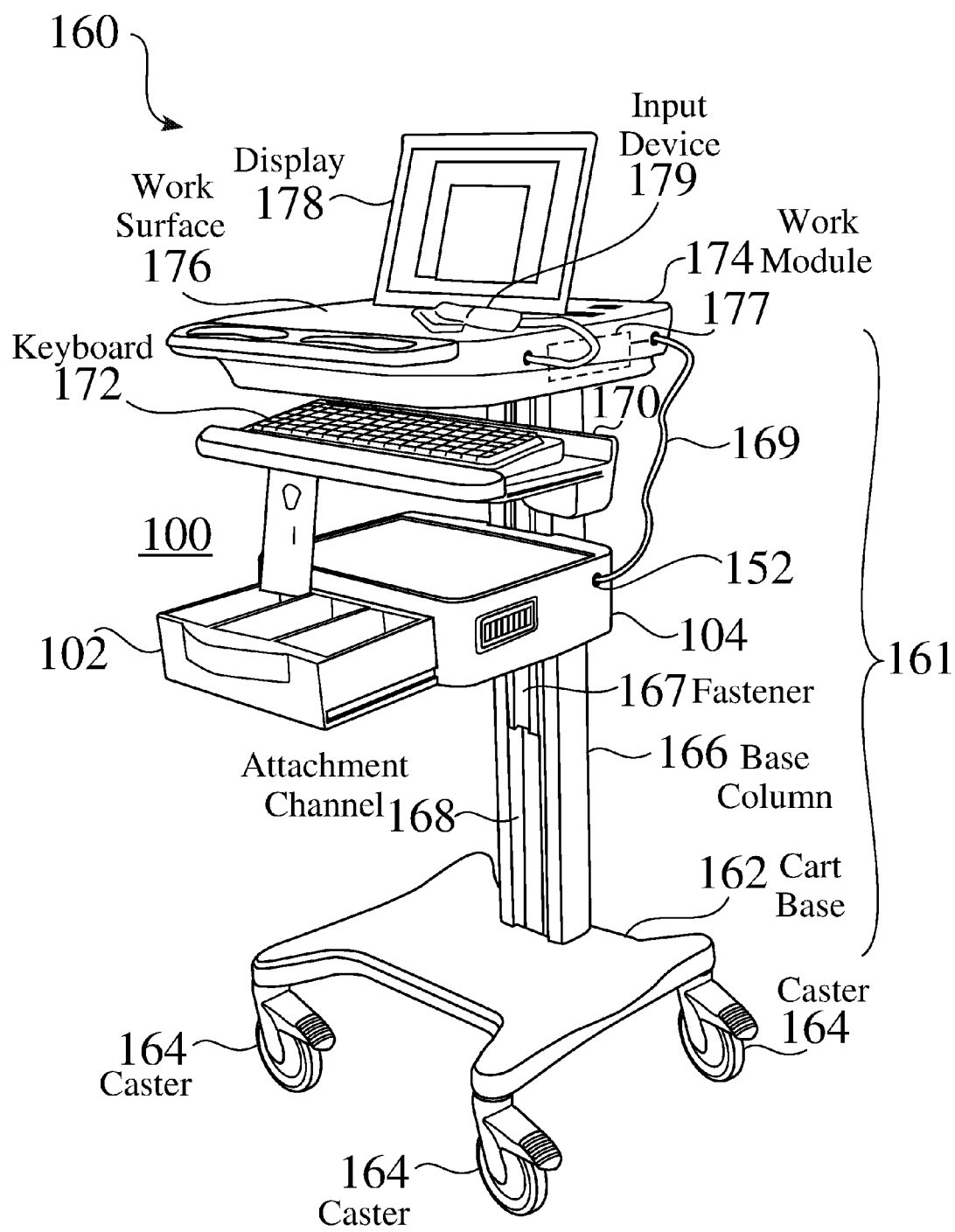
FIG. 5 shows a schematic view of a first exemplary embodiment of an enhanced medical dispensing drawer, wherein the enhanced drawer structure is attached to a medical cart having a channel, such as under a keyboard.

Some embodiments of the enhanced drawer 102 may preferably comprise an open interior 103, such as for but not limited to general storage for supplies, and may further comprise one or more dividers 24, such as but not limited to an acrylic, polycarbonate, or polystyrene divider system 22. For example, a large variety of supplies may be stored within an enhanced drawer structure 100 that is mounted to a mobile cart, e.g. 161 (FIG. 5). Exemplary supplies may comprise any of tongue depressors, swabs, wipes, razors, syringes, pens, gauze pads, papers, or reference materials. While such a standard drawer 102 may be lockable in some embodiments of the enhanced drawer structure 100, such as with a key lock 148, other drawers 102 may not be required to be locked 148. In some embodiments, the drawer structure 100 is configured such that the enhanced drawer 102 stays closed without the lock engaged.

The exemplary enhanced drawer 102 seen in FIG. 3 and FIG. 4 comprises a drawer interior 103, wherein one or more compartments 108, e.g. 108a-108c, may be defined by integrated dividers 106, and/or by additional divider components, e.g. such as but not limited to a divider system 22 having walls 24 and connectors 26.

The enhanced drawer 102 may further comprise compartment top covers 112 that correspond to one or more of the compartments 108. The compartment top covers 112 may be hinged 113 to be openable when the enhanced drawer 102 is in an open position 142o, and may be removable, such as for cleaning. The compartment covers 112 may preferably be clear or translucent, such that the user USR (FIG. 11), such as a nurse, doctor or clinician, may readily determine which of the compartments 108 are filled, and if so, which medications 302 (FIG. 11) or supplies are located within the compartment 108. One or more of the compartment covers 112 may further comprise markings or labels 119, and/or means 117 for receiving a label 119, e.g. such as an enclosure, window, or one or more slots to retain a label 119.

A compartment top cover 112 may be hingedly attached 113 to the top of a compartment 108, which is openable either when the drawer 102 is located in an open position 142o while installed in the drawer housing 104, or when the enhanced drawer 102 is removed from drawer housing 104. Compartment top covers 112 may preferably close with a snap fit, such as tightly enough to not open unintentionally, and to prevent medications 302 (FIG. 11) from falling out or from bouncing across dividers 106,24 if the enhanced drawer 102 is inverted or shaken.

The exemplary enhanced drawer 102 seen in FIG. 3 is slidably movable 141 with respect to the interior volume 120 of the drawer housing 104, such as with respect to runners 122, e.g. 122a,122b associated with the drawer housing 104. For example, the drawer runners 122a,122b may preferably correspond to the sides 105a,105b and/or to the bottom 107 of the enhanced drawer 102.

The exemplary enhanced drawer 102 seen in FIG. 3 and FIG. 4 also comprises a lock catch 114, wherein the latch 148 may be locked or unlocked when the drawer 102 is in the closed position 142c. While the exemplary lock catch 114 seen in FIG. 3 is shown on the bottom on a drawer side 105, e.g. 105a, the lock catch 114 may alternately be located at any position on the body of the enhanced drawer 102 with respect to a correspondingly located latch 148, such as at any of the side, bottom or rear of the enhanced drawer 102.

The enhanced drawer 102 may further comprise one or more drawer catches 116, such as on one or opposing sides 105 of the enhanced drawer 102, wherein the enhanced drawer 102 may preferably be prevented being removed entirely from the drawer housing 104, i.e. beyond the open position 142o, unless the user USR releases the catches 116. The user USR may thus remove an enhanced drawer 102, such as to load the enhanced drawer 102 at a pharmacy or at an ADC, to administer medications 302 within a tight room, or to administer medications 302 to patients PT (FIG. 13) that are in isolation.

Some embodiments of the enhanced drawers 102 may preferably comprise removable full height dividers 106, e.g. running front to rear, such as to divide the space into a maximum of three or four long areas 108. Dividers 106 may preferably extend across the whole length or width of the drawer 102, such as to prevent movement of medications, tools, or supplies between compartments 108 if the enhanced drawer 102 is inverted or shaken. In some embodiments, the dividers 106 are securely retained, such as with a snap fit or fastener.

Figure 6:
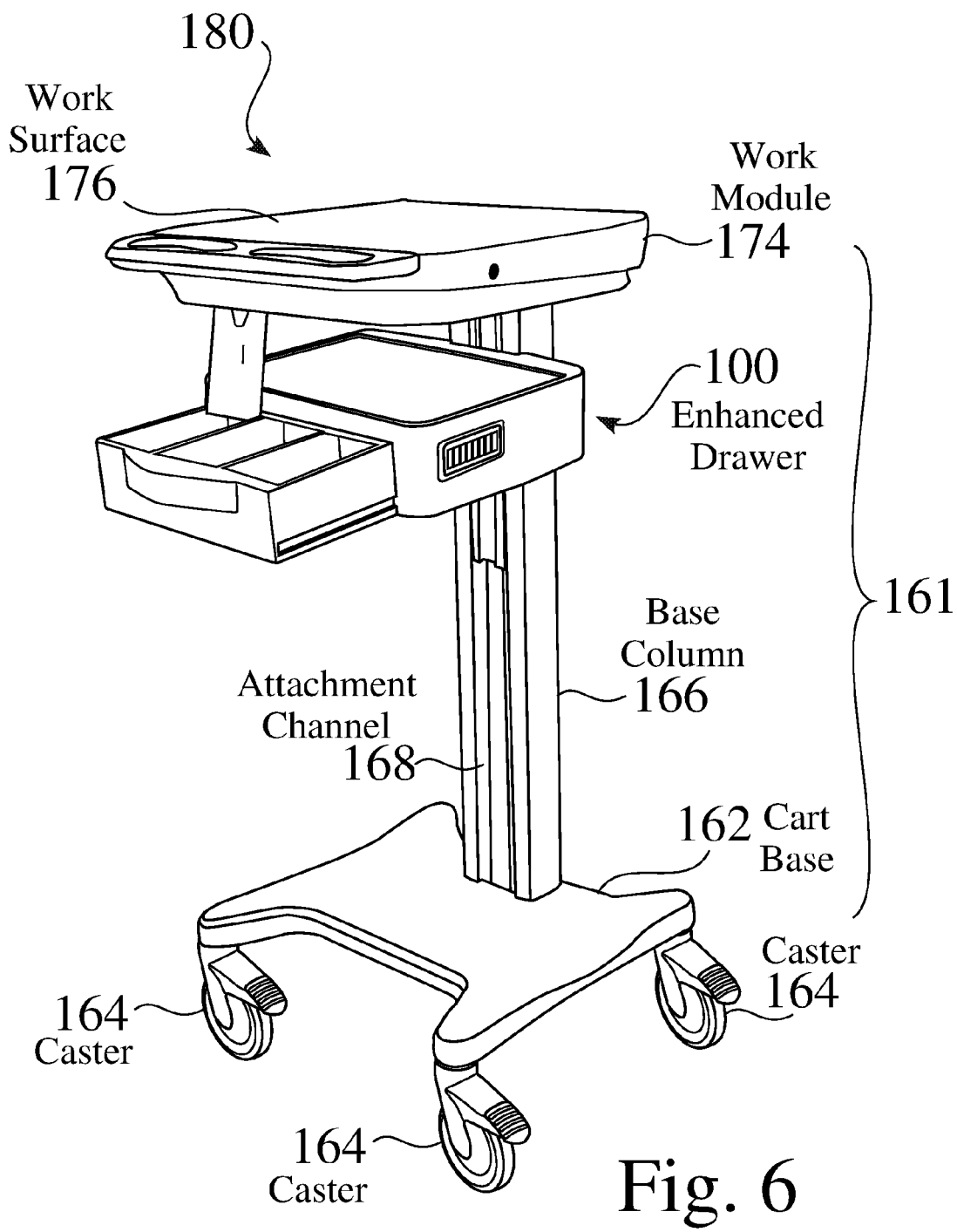
FIG. 6 shows a schematic view of a second exemplary embodiment of an enhanced medical dispensing drawer, wherein the enhanced drawer structure is attached to a medical cart having a channel, such as directly under a work surface module.

The enhanced drawer 102 may be configured to be highly cleanable. For example, the enhanced drawer 102 may comprise a material that is resistant to any of chemicals, cleaners, water, or elevated temperatures, wherein the enhanced drawer 102 may readily be removed and washed in a sink or dishwasher. In some embodiments, the enhanced drawer 102 comprises polypropylene (PP). The enhanced drawer 102 may also be designed to minimize any of gaps, ridges, or tight corners that may prevent thorough cleaning. In some embodiments, the enhanced drawer 102 comprises a single part, such as a single, seamless part having injection-molded construction. For example, the enhanced drawer 102 may preferably comprise a single gas counter☐pressure structural foam part, such as to match a top work module 174 (FIG. 5, FIG. 6).

The exemplary enhanced drawer structure 100 seen in FIG. 4 comprises a processor 144 and a corresponding memory 146, wherein the access pad 124, e.g. keypad 124a provides means for information entry 154, such as to allow a user USR to enter one or more characters 125 comprising an entered password or passcode 127 (FIG. 3), e.g. comprising letters, numbers, and/or symbols 125, or any combination thereof. One or more stored passcodes 154, e.g. 154a-154j, may be associated with an enhanced drawer structure 100, and are typically stored in the memory 146, wherein entry 402 (FIG. 15) of a passcode 127 by a user USR is compared 404 by the processor 144 to the stored passcodes 154, and if a match is made 404, the processor 144 unlocks the latch 148, allowing the drawer 102 to be opened 142o. If a match is not made, e.g. at a match determination step 404 (FIG. 15), the latch 148 is retained in a locked position, preventing access to the enhanced drawer 102.

The exemplary enhanced drawer structure 100 seen in FIG. 4 also comprises an input/output (I/O) data port 152 connected to the processor 144, e.g. such as but not limited to a UBS port 152. The I/O port 152 may preferably provide access, e.g. 236,242 (FIG. 10), to the processor 144, such as to controllably input, change, or delete one or more passcodes 154 stored in memory 146, and/or to export information regarding the operation of the enhanced drawer structure 100. For example, such information may comprise dates and times for drawer activities, such as but not limited to the filling of medications 302 into the enhanced drawer 102, times associated with locking or unlocking operations, drawer positions 142 based upon time, and/or passcode entry. Accessed information may preferably be downloaded and reviewed, such as to compare to assigned personnel USRs, hospital areas, work schedules, billing, and/or patients PT.

While some embodiments of the enhanced drawer structure 100 may be configured with a single stored passcode 154, other embodiments of the enhanced drawer structure 100 may be configured with a plurality of stored passcodes 154, e.g. 154a-154j, such as to provide a unique passcode 154 for a user USR or for a group of users USR. Embodiments 100 that are configured with a plurality of stored passcodes 154 may preferably provide tracking of the access to a drawer structure 100. For example, if a record indicates that a certain entered passcode 127 matched to a stored passcode 154 was used at a given time, this access to the drawer 100 may be attributed to an individual user USR that corresponds to the entered and recorded passcode 127, 154.

Alternately, if such an indicated user USR was not present at the time, the information may indicate that the entered and accepted passcode 127 may have been compromised, wherein the previously acceptable stored passcode 154 may be chosen to be deleted and/or changed.

The enhanced drawer structure 100 may automatically lock 408 (FIG. 15) when the enhanced drawer 102 is moved 141c (FIG. 12) from the open position 142o to the closed position 142c. As well, if the enhanced drawer structure 100 remains unlocked for a threshold period of time 410 (FIG. 15), the lock 148 may preferably be re-engaged automatically after the time threshold 156 is reached, e.g. after a set point of 30-60 seconds is reached. For example, as seen in FIG. 4, a time threshold 156, such as stored within a memory 146, may be established, e.g. through an I/O data port 152, and/or may comprise a preconfigured threshold value 156. In some embodiments, if the enhanced drawer 102 is left in a closed 142c and unlocked position, the latch 148 may preferably lock 410 after the time threshold 156 is reached.

The enhanced drawer housing 104 seen in FIG. 4 comprises different components associated with the security of the enhanced drawer structure 100, which may be integrated within an electronic key lock assembly 158, such as to provide an access pad 124, e.g. a keypad 124a or a card pad 124b (FIG. 16), connected to a processor 144, and having a corresponding memory 146. The electronic key lock 158 may also comprise a power source 159, such as a compartment to hold a replaceable or rechargeable battery. In some embodiments, the electronic key lock 158 comprises a Model No. DK-APH keylock module 158, available through Digilock by Security People, Inc., of Petaluma, Calif.

The enhanced drawer structure 100 may be configured for a wide variety of work environments, such as for but not limited to hospitals, laboratories, medical offices, retail or other business applications, or even for home applications. For example, the enhanced drawer structure 100 may be configured for a wide variety of hospital requirements and workflow, such as but not limited to:

- a secure slide☐out drawer structure that is mounted directly under a work surface module;
- a secure slide☐out drawer structure with that is mounted freestanding on a column, below a keyboard;
- a secure slide☐out drawer structure that is mounted freestanding on a column, with the top of the drawer housing 104 acting as a primary work surface;
- multiple secure slide☐out drawer structures 100 that are stacked with respect to each other; or
- a stationary secure drawer system within a medical environment.

Different enhanced drawers 102 may preferably be configured for different system configurations 100. For example, some enhanced drawer structures 100 may comprise an open enhanced drawer 102, such as having a single compartment 106 defined within the drawer interior 103. An open drawer configuration may preferably be slidable 141o (FIG. 13) from a closed position 142c to an open position 1042o, wherein at the open position 142o, a rear portion, e.g. 3 inches, of the drawer 102, is still retained within the drawer housing 104. At this position 142o, the user USR may controllably press the drawer catch(es) 114, such as located on the side or bottom 107 of the enhanced drawer 102, to remove the enhanced drawer 102 entirely from the housing 104. Other enhanced drawers 102 may further comprise any of dividers 106 or covers 112, such as for dispensing of medications 302 or other medical supplies. While different embodiments of the enhanced drawer 102 may preferably be removable from the housing 104, some drawer structures 100, such as for medical dispensing, may be configured as free standing enclosures that can load, hold, and administer medications 302, and be docked securely in the drawer housing 104.

FIG. 5 is a schematic view of an exemplary embodiment of an enhanced medical dispensing drawer 100, wherein the enhanced drawer structure 100 is attached to a medical cart 161 having a base column 166, such as under a keyboard 172. For example, an exemplary cart 161 may comprise a base column 166 attached to a cart base 162 having a plurality of casters 164, wherein the cart 161 comprises means 168 for attaching one or more different modules to the base column 166, such as but not limited to the enhanced drawer structure 100, a work module 174, and/or a keyboard module 170. In some embodiments, the cart 161 comprises a variable height rolling cart (VHRC), such as available through GCX Corp., of Petaluma, Calif.

The exemplary enhanced drawer structure 100 seen in FIG. 5 may preferably be affixed to the base column 166 though one or more intermediate fastener components 167. For example, the enhanced drawer structure 100 may be fastened 147 (FIG. 4) to an intermediate bracket 143 (FIG. 4) that is fixedly retained within an attachment channel 168. The associated fastener components 167 may preferably be concealed or hidden, such as to prevent unwanted access and be resistant to tampering. In some embodiments, the fasteners 167 that mount the drawer housing 104 to the base column 166 are hidden and inaccessible when the drawer 102 is in the closed/locked position 142c.

The cart 161 seen in FIG. 5 provides a versatile apparatus that may readily be moved by the user USR within the work environment, such as for loading, transporting, and dispensing medications 302. The work module 174 seen in FIG. 5 may preferably comprise a processor 177 linked with a display 178 and to an input device, e.g. a keyboard 172, wherein the user USR may input and view information. Additional devices 179 or equipment may preferably be attached to the work module 174, such as but not limited to:

- a bar code reader 179, e.g. for reading medication 302 or patient identification codes 322 (FIG. 12); and/or
- test or monitoring apparatus, e.g. such as but not limited to any of blood pressure, pulse, blood sugar, temperature, or flow.

As seen in FIG. 5, the enhanced drawer structure 100 may preferably be sized to compliment the footprint of the structures it is attached to, such that a cart 161 may readily be moved throughout a facility, as well as into, out of, and around rooms within a hospital. For example, some current drawer housings 104 comprise a width of about 10 to 12 inches, a height of about 3 to 3.5 inches, and a depth of about 8 to 10 inches. During an exemplary process of delivering and administering medications 302, the user USR of the cart 161 and enhanced drawer structure 100 seen in FIG. 5 may readily enter 262 (FIG. 11) medication information and/or patient information, such as with a bar code reader 179, and can easily view the display 178, which may provide patient chart information, and may further display any alarms or notes associated with the coding step 262.

As also seen in FIG. 5, the data port 152 of the enhanced drawer 100 may be connected to the processor 177 of the work module 174 or to another terminal, such as by a USB cord 169, wherein information may readily be transferred into or out of the enhanced drawer structure 100. For example, a work module 174 may be connected to at least one other computer, such as an administrative computer, e.g. 344 (FIG. 14), at the medical facility, over a wired or wireless network. Information regarding the operation of the enhanced drawer 100 may therefore be logged 240 (FIG. 10) by the work module 174, and/or may be transferred 412 (FIG. 15) to other computers. Similarly, information may be sent from an administrative computer through the work module 174, such as to securely update passcodes 154, or to lock down an enhanced drawer structure 100 if necessary, e.g. to prevent access to medications 302.

Figure 7:
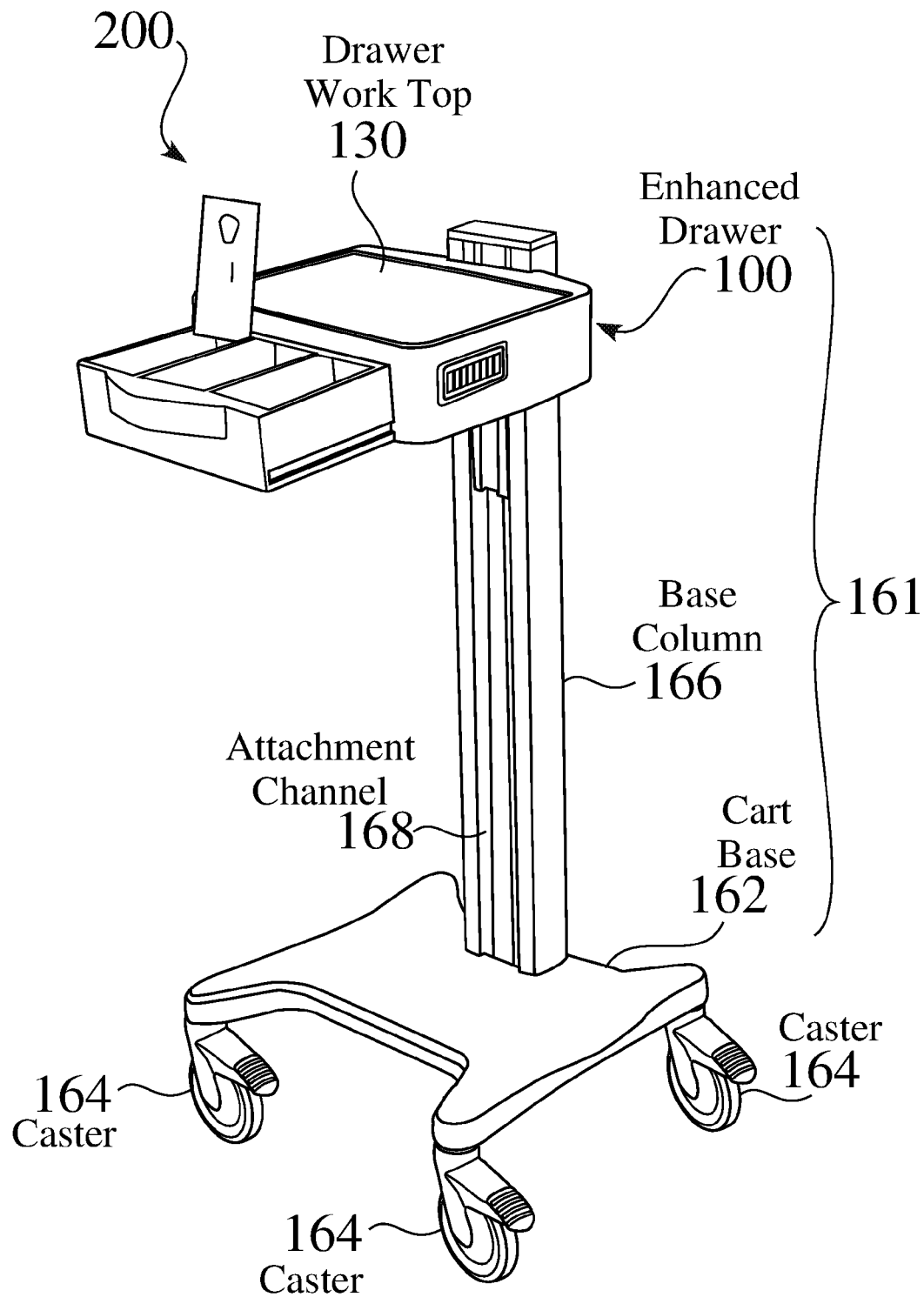
FIG. 7 shows a schematic view of an exemplary embodiment of an enhanced medical dispensing drawer, wherein the enhanced drawer structure is mounted to a medical cart, and wherein the worktop of the drawer housing comprises a primary work surface for the cart.

FIG. 6 shows a schematic view 180 of an exemplary embodiment of an enhanced medical dispensing drawer structure 100, wherein the enhanced drawer structure 100 is mounted to a base column 166 of a medical cart 161, directly under a work module 174 having a work surface 176. FIG. 7 shows a schematic view 200 of an exemplary embodiment of an enhanced medical dispensing drawer structure 100, wherein the enhanced drawer structure 100 is free-standingly mounted to a base column 166 of a medical cart 161, and wherein the worktop 130 of the drawer housing 104 comprises a primary work surface for the cart system 161, such as for but not limited to administration of drugs, updating charts, or writing notes. In some embodiments of the enhanced drawer structure 100, the drawer housing 104 has a load capacity of about 10 pounds, such as to provide a worktop 130 that has adequate stiffness for writing. For some embodiments of the enhanced modular drawer structure 100, the drawer housing 104 has a rated maximum allowable deflection of less than ⅜ inch for a load of 25 pounds. The drawer housing 104 may further comprise a ridge 132 (FIG. 3) that extends around the perimeter of the worktop 130, such as to retain any of medications 302, supplies, writing implements, spills, or small objects.

Figure 8:
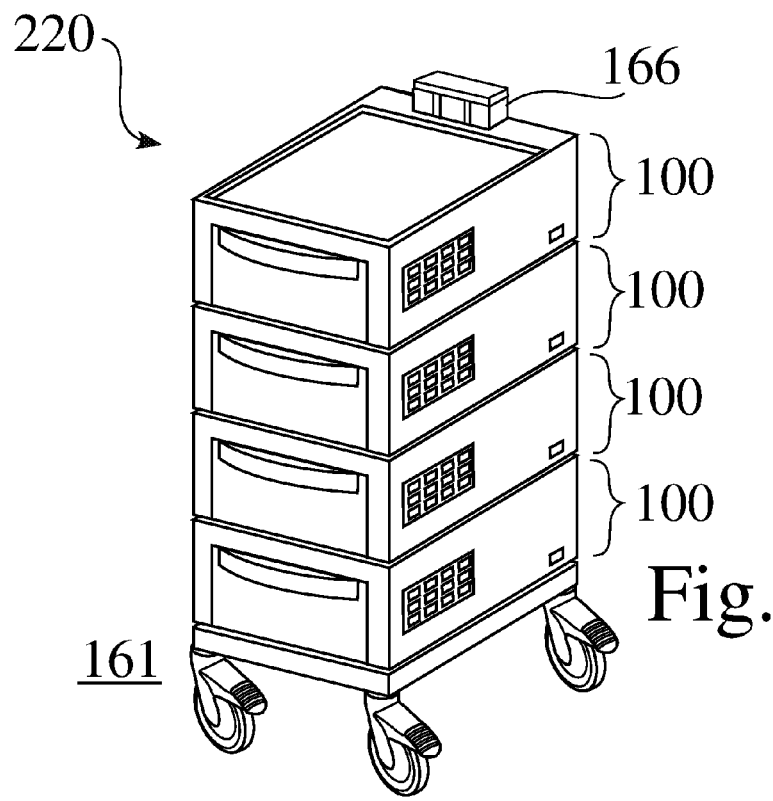
FIG. 8 shows a schematic view of an exemplary embodiment of a plurality of enhanced medical dispensing drawers mounted to a base column of a cart structure.
Figure 13:
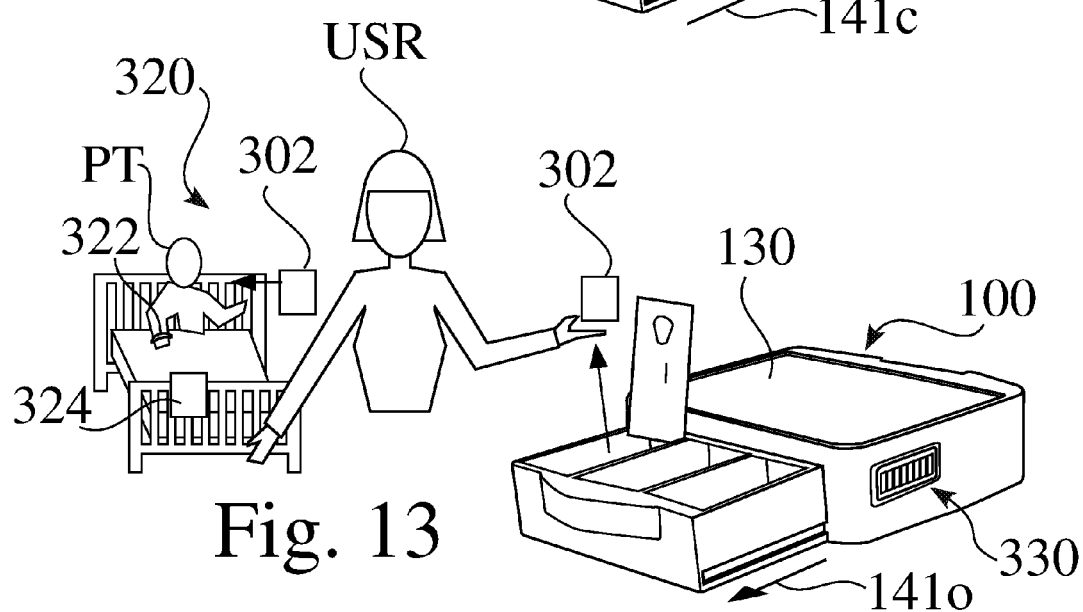
FIG. 13 is a schematic view of a nurse dispensing medications from an enhanced medical dispensing drawer.

FIG. 8 shows a schematic view 220 of an exemplary embodiment of a plurality of enhanced medical dispensing drawers 100 mounted to a base column 166 of a cart structure 161, such as to provide access for one or more patients PT (FIG. 13). Some embodiments of enhanced medical dispensing drawer structures 100 may be stackable, such as by comprising interlocking surfaces, e.g. the worktop 130 of a first enhanced drawer 100 may have a profile that corresponds to a generally mating profile of the bottom of a housing 104 for a second enhanced drawer 100.

Figure 9:
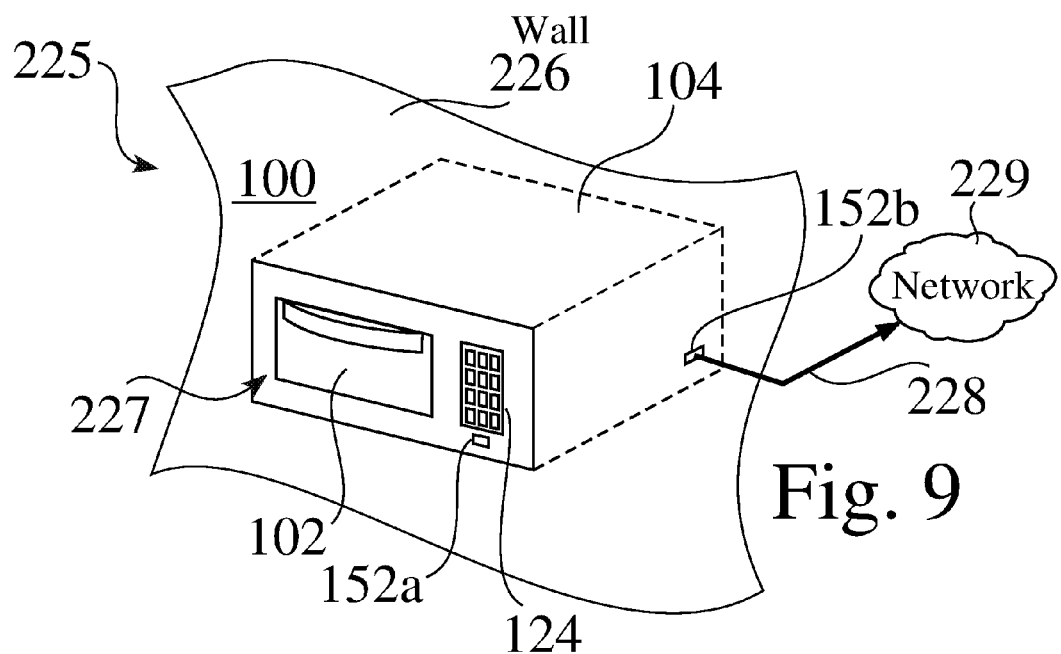
FIG. 9 shows a schematic view of an exemplary embodiment of an alternate enhanced medical dispensing drawer, such as to provide a wall mounted dispensing structure.

FIG. 9 is a schematic view 225 of an exemplary embodiment of an alternate enhanced medical dispensing drawer structure 100, such as to provide a secure wall drawer 102 for mounted storage and/or dispensing. The drawer housing 104 seen in FIG. 9 is mountable directly to or within a wall 226, wherein the access pad 124 is located on the front face of the housing 104. As seen in FIG. 9, the data port 152, e.g. 152a, may also be located on the front housing face 227, or may alternately be connected elsewhere, e.g. 152b, with respect to the housing 104, e.g. such as hard wired 228 to a computer network 229. The enhanced medical dispensing drawer structure 100 seen in FIG. 9 may be preloaded by hospital personnel USR, wherein the drawer 100 provides medications 302 and/or supplies that are easily accessed in situ, such as for but not limited to emergency conditions, wherein a nurse or doctor USR may need immediate secure access to medications 302 or supplies for a patient PT.

Figure 10:
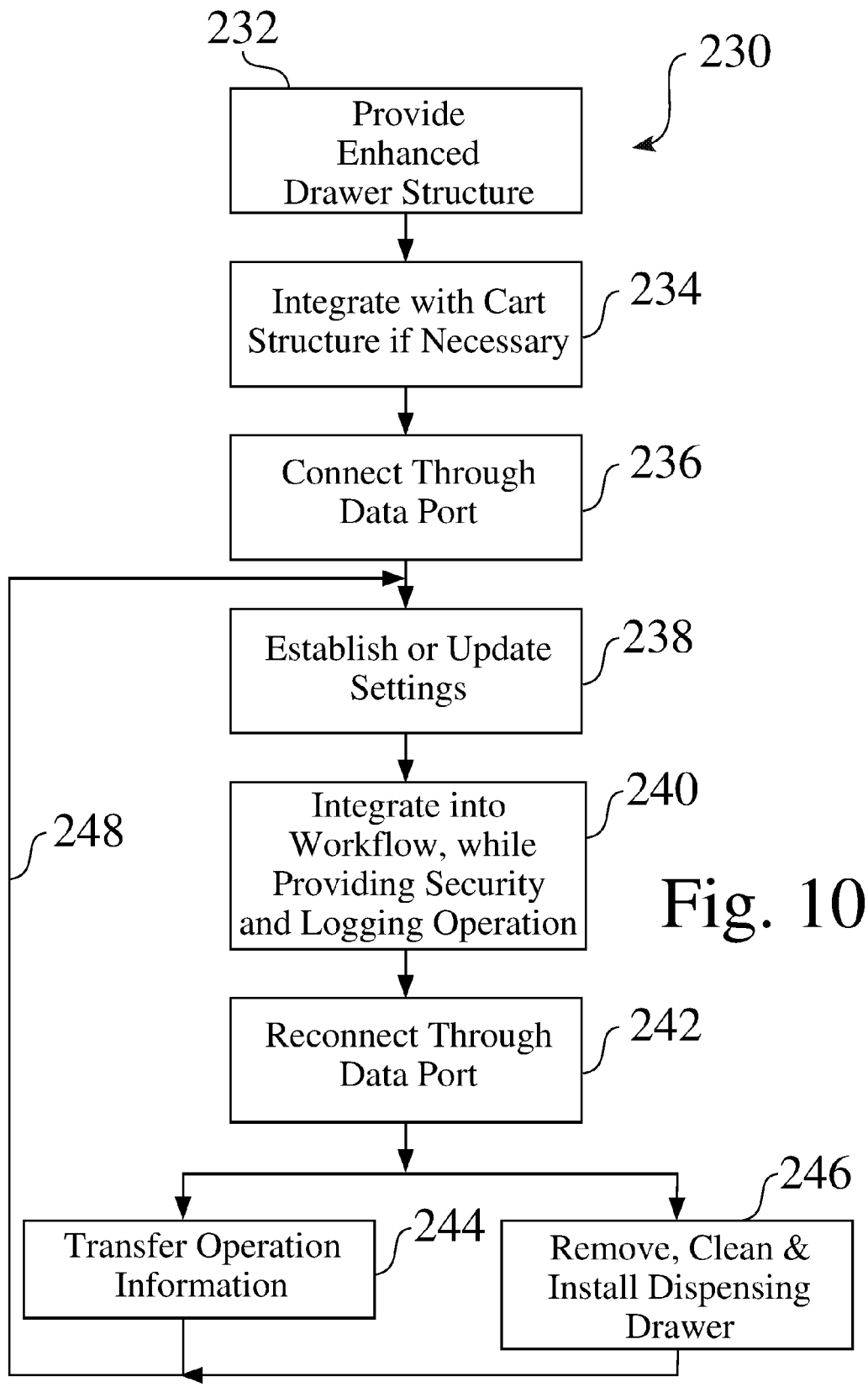
FIG. 10 shows an exemplary process of placing the enhanced drawer structure into service, such as with setting control, and/or logging, and downloading of operation data.

FIG. 10 shows an exemplary process 230 for placing an enhanced drawer structure 100 into service, such as with setting control, logging, and downloading of operation data. For example, an enhanced drawer structure 100 may be provided 232, and may further be integrated 234 into a delivery structure, such as a cart structure 161. A connection may then be made 236 to the data port 152 of the enhanced drawer structure 100, such as to establish settings if necessary, e.g. to assign passcodes 154 that are unique to a user or work group. The enhanced draw structure 100 may then be integrated 240 into a workflow, e.g. a workflow process 250 (FIG. 11), such as to provide secure storage, transport, and dispensing of medications 302. Based upon system configurations, the enhanced drawer structure 100 may be reconnected 242 through the data port 152 if necessary, such as during workflow through a work module 174, or after workflow, through connection 242 to another terminal 344 (FIG. 14), wherein operation information may be downloaded 244 from the memory 146 through the processor 144. As desired, the enhanced drawer 102 may preferably be removed, cleaned, and reinstalled 246. The enhanced drawer structure 100 may then be returned 248 to service, such as to update any settings 238, before entering a new workflow 240.

Figure 11:
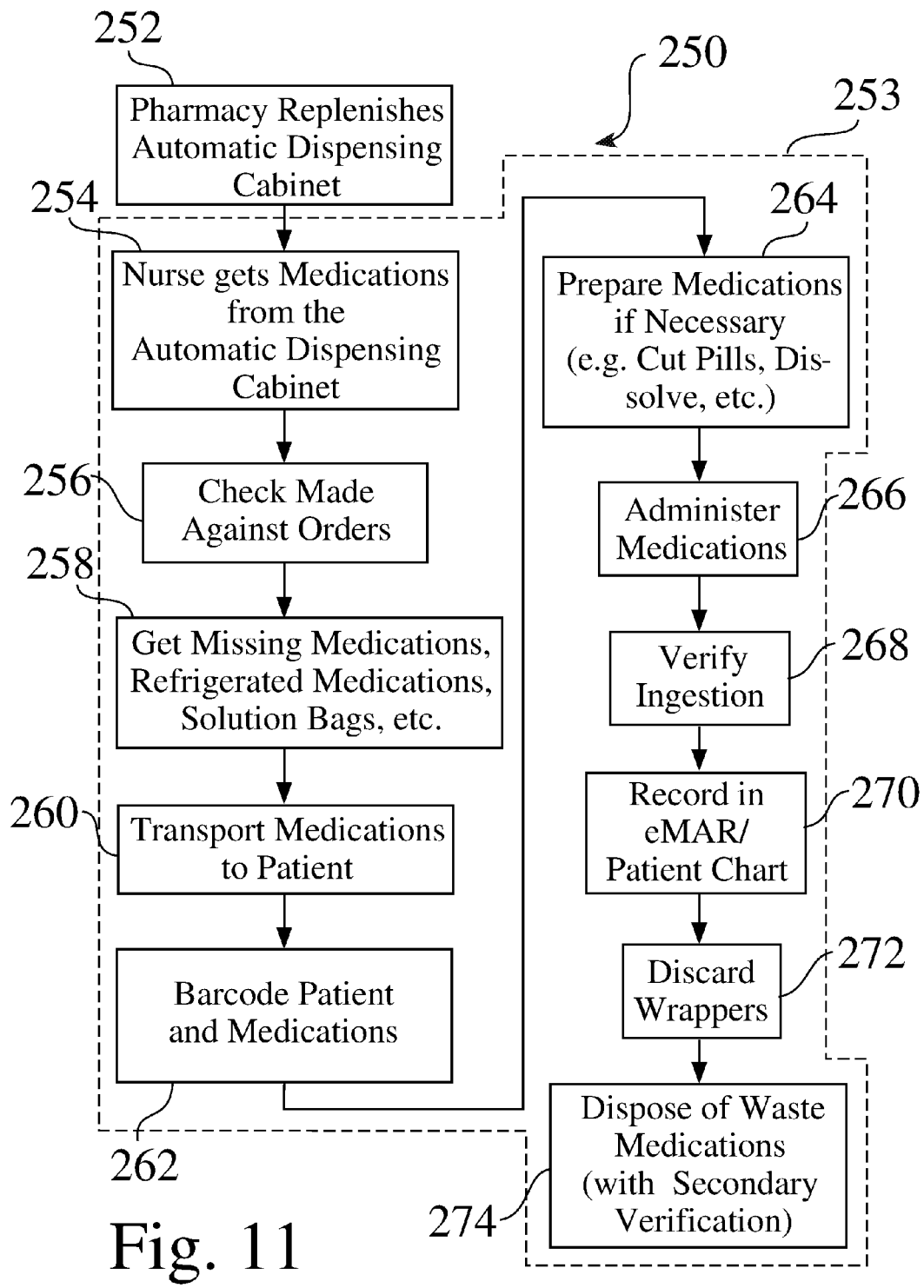
FIG. 11 shows an exemplary process for dispensing medications with an enhanced medical dispensing drawer.
Figure 12:
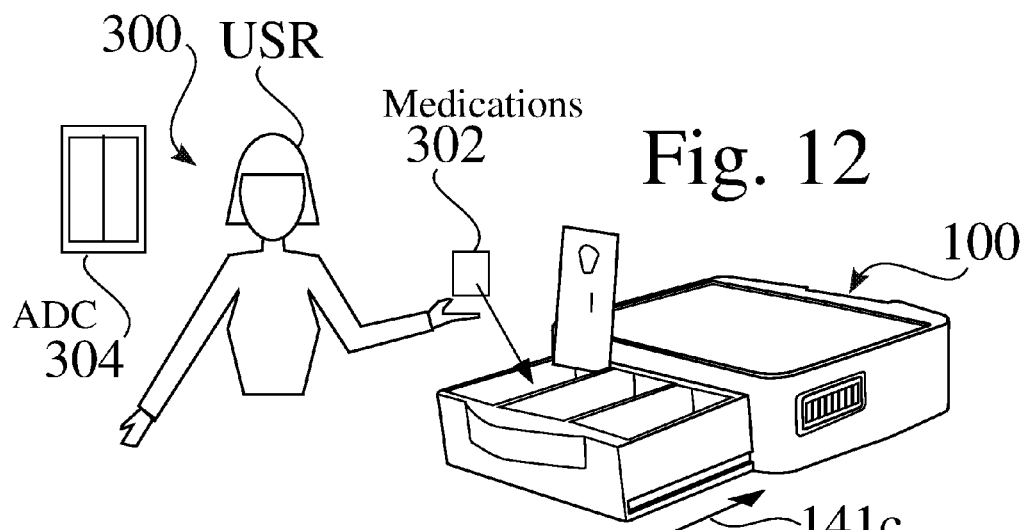
FIG. 12 is a schematic view of a nurse filling an enhanced medical dispensing drawer.
Figure 14:
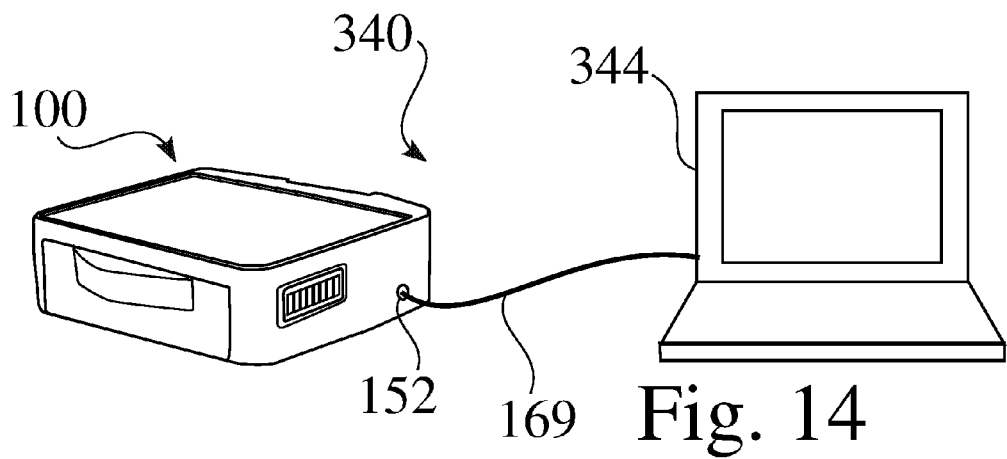
FIG. 14 is a schematic view of a data connection with an enhanced medical dispensing drawer.
Figure 15:
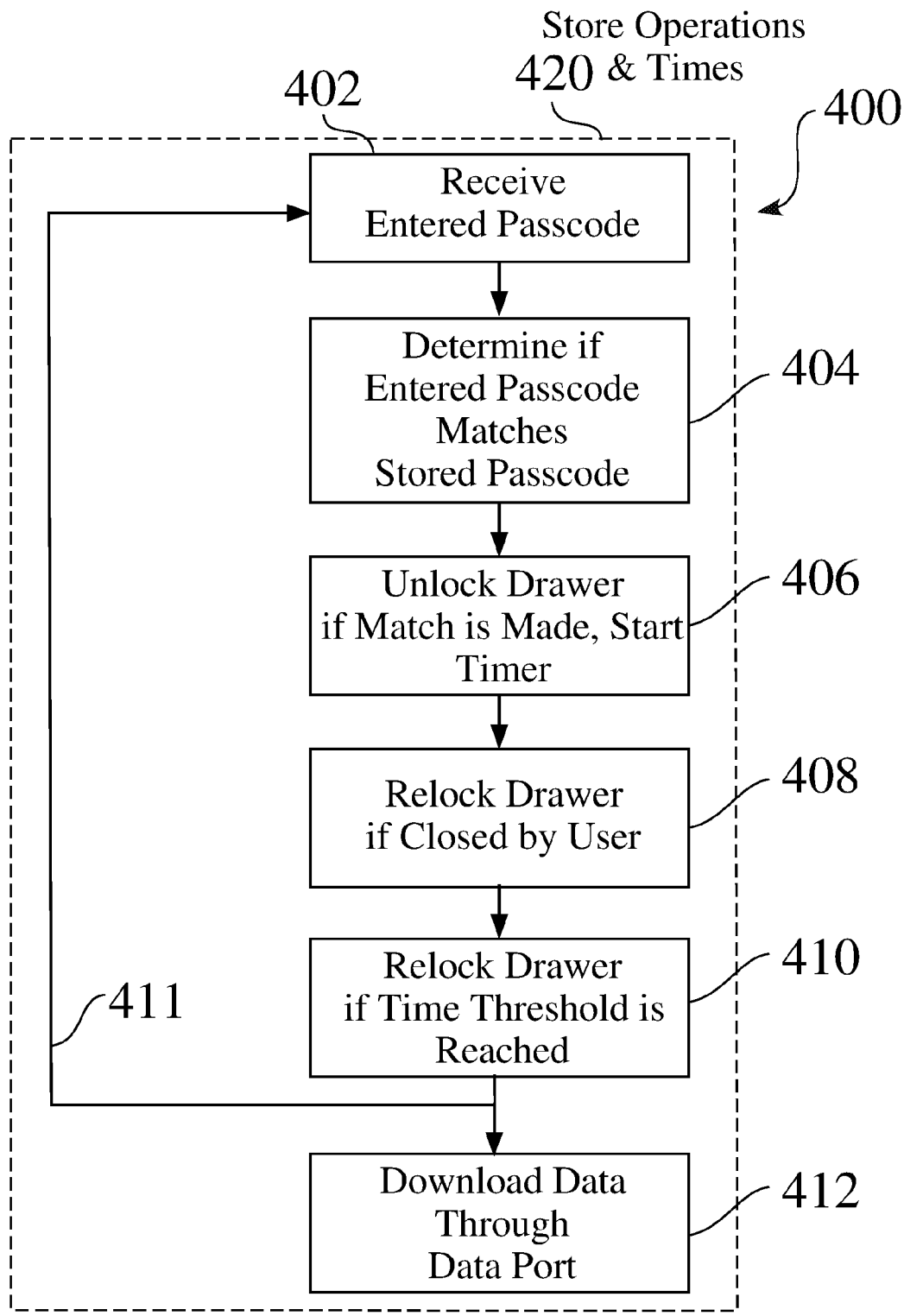
FIG. 15 shows an exemplary process of providing secure access, logging operations, and data transfer for an enhanced drawer structure.

FIG. 11 is a flowchart of an exemplary process 250 for loading, transporting, and dispensing medications 302 (FIG. 13) with an enhanced medical dispensing drawer structure 100. The enhanced drawer structure 100 provides enhanced security 253 throughout a large portion of the workflow 250 for a nurse or clinician user USR. FIG. 12 is a schematic view 300 of a nurse USR filling an enhanced medical dispensing drawer structure 100, wherein the nurse USR may readily close 141c and lock the enhanced drawer 102 after filling. FIG. 13 is a schematic view 320 of a nurse USR entering 330 a passcode 154 to open 141o and dispense medications 302 from an enhanced medical dispensing drawer structure 100. FIG. 14 is a schematic view 340 of a data connection 169 with an enhanced medical dispensing drawer structure 100. FIG. 15 shows an exemplary process 400 for providing secure access of logging operations and for data transfer through an enhanced drawer structure 100.

As seen in FIG. 11, a pharmacy may typically fill or replenish 252 an automated dispensing cabinet (ADC) 304 (FIG. 12), which may be located in a separate room that is otherwise locked. A nurse USR with an enhanced drawer structure 100, such as with a cart 161, then gets 254 the medications 302 from the automated dispensing cabinet 304, such as for one or more patients PT, and checks 256 the medications against orders. During the acquisition 254 of the medications 302 from an ADC 304, the nurse USR typically keys data associated with the patient PT, and the ADC 304 dispenses the appropriate medications, such as within single-dose kits. Once the kits of medications 302 are stored within the enhanced drawer 102 and the drawer is closed 142c, the drawer structure 100 provides security for transport 260 to the patient PT, even if the drawer structure 100 is left unattended, since the nurse USR is required to enter a valid passcode 154 to open the drawer 102.

While the process 250 seen in FIG. 11 shows interaction with an automated dispensing cabinet 304, it should be understood that the enhanced drawer structure may alternately be used for other possible workflows, such as but not limited to direct receipt of medications 302 from a pharmacy by the nurse, or filling of the enhanced drawer 100 by a pharmacy or by other personnel. For example, the pharmacy may have direct access to the enhanced drawer structure 100, such as with a unique passcode 154 associated with one or more users at the pharmacy, to fill the drawer 100 directly.

As also seen in FIG. 11, the nurse USR may proceed 258 as needed to get any missing medications, refrigerated medications, and/or solution bags, etc., and then transports 260 the enhanced drawer structure 100, loaded with medications 302, to a patient PT (FIG. 13). The nurse USR then typically bar codes 262 both the patient PT, e.g. having an identification bracelet 322 (FIG. 13), and the medications 302, such as to provide inventory control and prevent human errors. The nurse USR then prepares 264 the medications 302 if necessary, such as but not limited to cutting pills, and/or dissolving medications 302 in water. The nurse USR then administers 266 the medications 302, verifies 268 ingestion of the medications 302, and makes 270 an electronic medication record, such as associated with the patient chart 324 (FIG. 12). The nurse USR then typically discards 272 any wrappers if needed, and may dispose 274 any waste medications 302, such as with secondary verification.

In the exemplary process seen in FIG. 11, the enhanced drawer structure 100 provides security 253 throughout many steps associated with the acquisition, transport, administration and logging of medications. As seen in FIG. 14, the enhanced drawer structure 100 is connectable to another computer or terminal 344, such as by a cable 169 connected through the data port 152. As such, the enhanced drawer structure 100 may be readily updated or otherwise synchronized 238 (FIG. 10), such as:

before a workflow process 240 (FIG. 10) has begun;
during work, such as in conjunction with coding patients and medications, administration of medications, or charting; and/or
after a work flow process 240 as been completed, e.g. during or at the end of a shift.

The enhanced draw structure 100, such as in combination with a work cart system 161, can therefore provide secure storage for a wide variety of hospital settings, such as but not limited to emergency departments (ED), intensive care units (ICU), operating rooms (OR), recovery areas, or other hospital rooms. A cart 161, having one or more enhanced drawer structures 100 may readily be used for any of bedside charting, medication administration, or as a remote workstation, while providing secure storage for a wide variety of materials, such as but not limited to any of:

medications 302
general use supplies (tongue depressors, cleaning supplies, etc.);
papers; or
reference materials.

The enhanced draw structure 100 can readily be mounted at any point along a base column 166, such as vertically along an attachment channel 168 (FIG. 5). Alternate embodiments of the enhanced draw structure 100 may be mounted vertically on the rear of a column structure 166, e.g. such as with the drawer 102 opening to the side of the cart 161.

As seen in FIG. 15, the enhanced drawer structure 100, such as during a workflow process 240 (FIG. 10), may receive 402 an entered passcode 127 through the keypad 124, such as entered by an authorized user USR. The processor 144 determines 404 if the entered passcode 127 matches a currently stored, i.e. acceptable passcode 154. If so, the processor 144 sends a signal or otherwise allows the latch 148 to unlock the drawer 102, while a timer 145 (FIG. 4) is started. If the user USR opens the unlocked drawer 102, such as to dispense medications 302, once the drawer is closed 141c by the user USR, the processor 144 may preferably automatically relock the latch 148, wherein the user USR is then required 411 to reenter 402 a passcode 127. In some system embodiments 100, the processor 144 may relock the drawer 102 if a time threshold 156 (FIG. 4) is reached before the enhanced drawer 102 is opened by the user USR. As also seen in FIG. 15, operation data may be downloaded 412 through the data port 152.

FIG. 16 is a simplified functional schematic view 420 of an alternate enhanced drawer structure 100, e.g. 100b. The enhanced drawer structure 100 seen in FIG. 16 comprises a lock or latch 148 that is controllably activated through an access pad 124, such as a keyless entry module 124, e.g. a card swipe pad 124b, wherein one or more access cards 427 provide secure keyless access to the enhanced drawer structure 100, without requiring a mechanical key.

The card swipe pad 124b seen in FIG. 16 allows a user USR to input encoded information from an access card 427, such as by sliding or inserting the access card 427 through a card reader slot 425. The access card 427 includes an electronic or a radio frequency identification (RFID) passcode 154, such as uniquely assigned to a user USR or a group of USRs. When the card 427 is swiped through the card reader slot 425, the encoded passcode 154 is read and compared 404 by the processor 144 to the stored passcodes 154, and if a match is made 404, the processor 144 unlocks the latch 148, allowing the drawer 102 to be opened 142o. If a match is not made, e.g. 405 (FIG. 10), the latch 148 is retained in a locked position, preventing access to the enhanced drawer 102.

The enhanced drawer structure 100, such as the enhanced structure 100b seen in FIG. 16, may preferably comprise means for data transfer, such as comprising an input/output (I/O) data port 152 and/or a master key data transfer 430 connected to the processor 144. Master key data access 430 may preferably be used either alone, or in conjunction with a data port 152. For example, the I/O data port 152 and/or the master key data access 430 may provide access, e.g. 236,242 (FIG. 10), to the processor 144, such as to controllably input, change, or delete one or more passcodes 154 stored in memory 146, and/or to export information regarding the operation of the enhanced drawer structure 100.

The enhanced drawer structure 100, e.g. 100b, may also comprise a key override 432 to provide access to an enhanced drawer 102, such as linked through the processor, or linked directly to the latch 148. For example, in a situation where an electronic lock 158 fails or dies, operation of the key override 432, such as comprising a mechanical key, may provide immediate access to critical medications 302.

Figure 17:
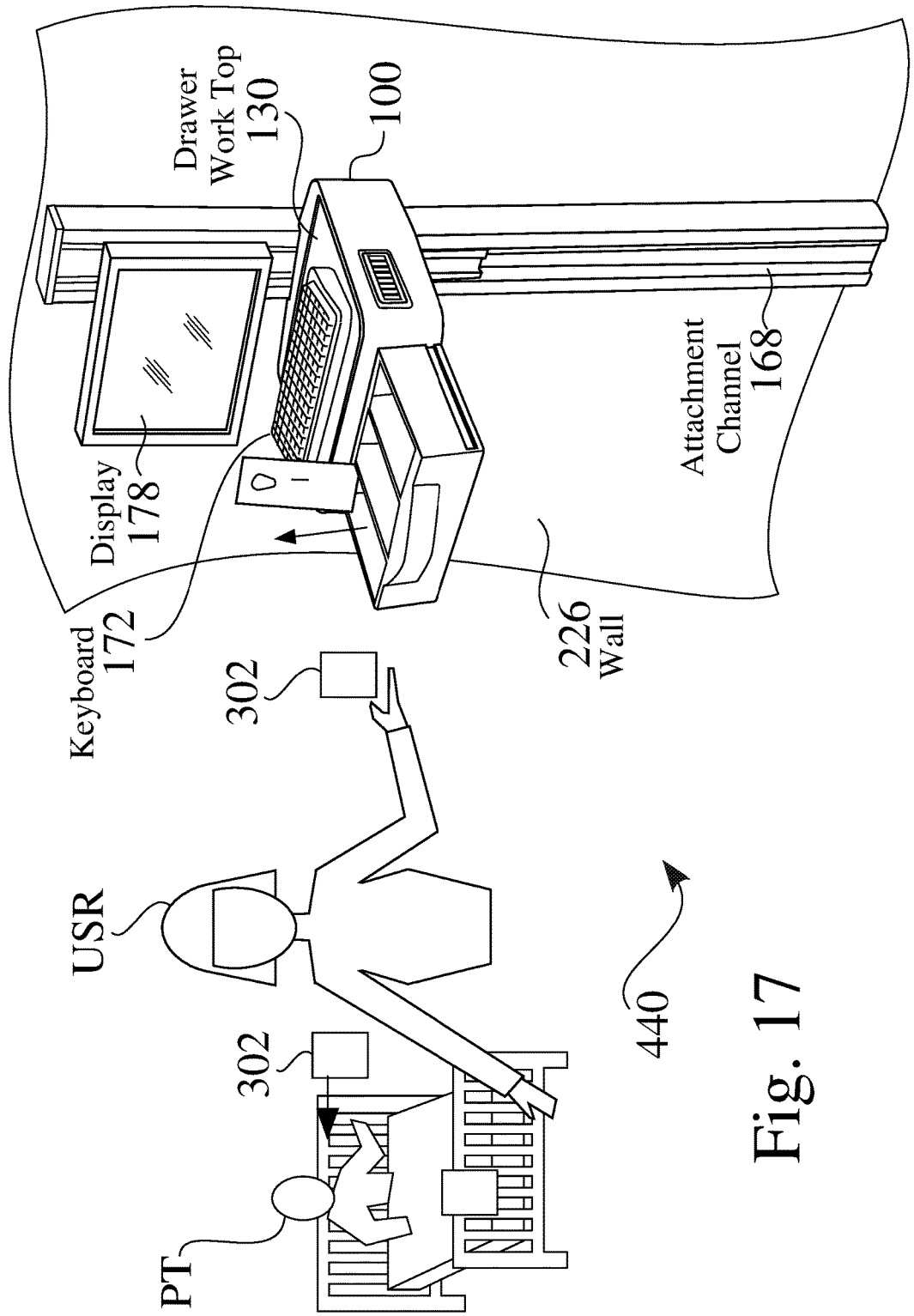
FIG. 17 shows a schematic view of an exemplary embodiment of an enhanced medical dispensing drawer that is mounted externally to a wall, such as to provide a work surface.

FIG. 17 shows a schematic view 440 of an exemplary embodiment of an enhanced medical dispensing drawer structure 100 that is mounted externally to a wall 100, such as to provide a work surface 130. The enhanced drawer structure 100 seen in FIG. 17 is connected to a wall 226, such as through an attachment channel 168. The structure extends from, i.e. protrudes, from the wall 226, wherein the work surface 130 may be used by the nurse USR, such as in conjunction with a wall-mounted flat panel display 178. The work surface 130 provides room for any of a keyboard 172, charts, and/or preparation of medications 302.

Figure 18:
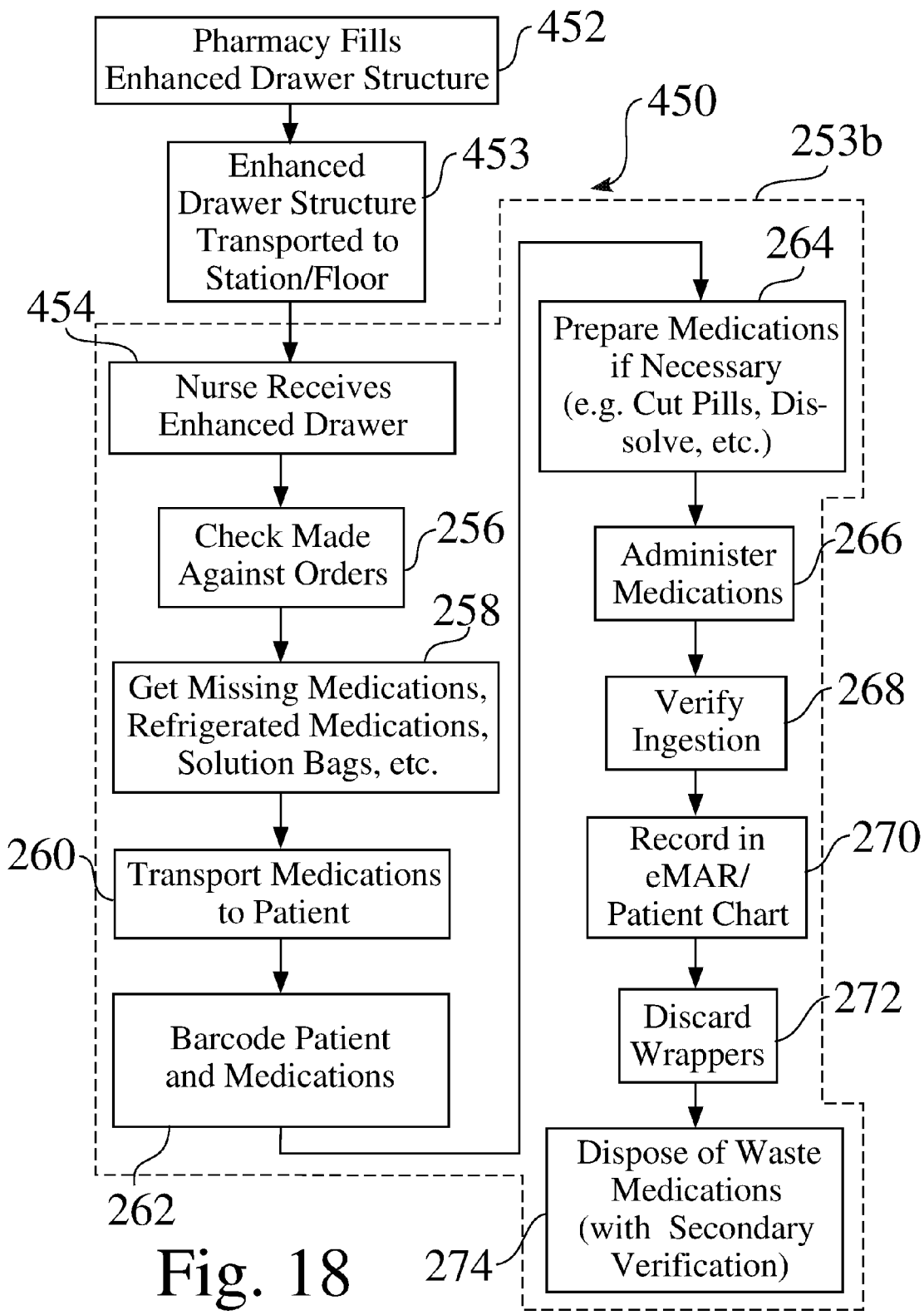
FIG. 18 shows an alternate workflow process, wherein medications are transferred within one or more enhanced medical dispensing drawers to a secondary area, such as to be docked into carts or a wall unit, before dispensing.

FIG. 18 shows an alternate workflow process 450, wherein a pharmacy fills 452 one or more enhanced drawer structures 100 with medications 302. The pharmacy or other personnel may then transport 453 one or more of the enhanced drawer structures 100, such as to an area, station, or floor, where they are received 454 by one or more nurses USRs. Several enhanced drawer structures 100 may preferably be transported 453, such as on a trolley, or on a stacked drawer structure 220 (FIG. 8). Once the enhanced drawer structures 100 arrive at the delivery area, station, or floor, the enhanced drawer structures 100 may preferably be securely docked for receipt 454, such as within a cart 161 or in a wall unit, e.g. 225 (FIG. 9, FIG. 17).

The enhanced drawer structure 100 therefore readily provides enhanced security throughout a wide variety of environments and workflows. The matching of entered passcodes 127 to stored passcodes 154 does not require mechanical keys that are easily lost or duplicated. As well, the stored passcodes 154 may provide traceability to individual users.

Furthermore, operational data is readily collected and downloaded through the data interface 152. The enhanced drawer structure 100 may provide a "dead latch" 408 that locks automatically when the door is closed, and/or may relock 410 automatically if the drawer 102 is left unlocked for a time that meets or exceeds a stored time threshold 156.

While the enhanced drawer structure and methods of use are described herein in connection with hospital settings, the drawer structure is not necessarily limited to storage and dispensing of medications and/or medical supplies, and may alternately be used for any of storage, access, and distribution for a wide variety of items, in a wide variety of environments.

As well, while the exemplary enhanced drawer structure and methods of use are described herein in connection with access pads, such as keypads and card readers, it should be understood that other mechanisms for secure keyless access may readily be integrated with the enhanced drawer structures and methods, such as but not limited to fingerprint scanners, retina scanners, and/or facial recognition.

Accordingly, although the invention has been described in detail with reference to a particular preferred embodiment, persons possessing ordinary skill in the art to which this invention pertains will appreciate that various modifications and enhancements may be made without departing from the spirit and scope of the claims that follow.

What is claimed:

1. An apparatus comprising:
   a base column that extends upward from a first end to a second end and that includes an attachment channel defined therein;
   a plurality of spaced attachment points that are located along the attachment channel and configured to receive and secure thereto drawer housings;
   a plurality of drawer housings,
      where each drawer housing is fixedly attachable to the base column through the attachment channel,
      where a drawer opening extends inward from a front end of each drawer housing to define an interior volume, and
      where each drawer housing includes a lock and a processor;
   a plurality of drawers that each include one or more compartments,
      where each drawer is slidably movable with respect to the interior volume of the corresponding drawer housing between
         a closed position in which the compartments are inaccessible, and
         an open position in which the compartments are at least partially accessible; and
   a plurality of access pads mounted to the plurality of drawer housings for entry of a passcode by a user,
   wherein each processor is configured to unlock the corresponding lock when the passcode matches a stored passcode value for the corresponding drawer housing.

2. The apparatus of claim 1, wherein the plurality of access pads comprises keypads, card readers, fingerprint scanners, retina scanners, facial recognition systems, or some combination thereof.

3. The apparatus of claim 1, wherein each drawer housing comprises a substantially planar upper surface.

4. The apparatus of claim 3, wherein a ridge extends upward from the substantially planar upper surface around a periphery of each drawer housing, and wherein the ridge is configured to retain any of medications, supplies, writing implements, spills, or small objects.

5. The apparatus of claim 1, wherein each drawer housing comprises a memory that includes the stored passcode value.

6. The apparatus of claim 1, wherein each drawer housing comprises a data port that is connected to the processor.

7. The apparatus of claim 6, wherein each processor is configured to send information through the data port to an external computer.

8. A drawer assembly comprising:
   a drawer housing having
      a drawer opening that extends inward from a front end of the drawer housing to define an interior volume, and
      a notch along a back end of the drawer housing to define an attachment channel,
      where the drawer housing includes
         one or more fastener components for securing the drawer housing to an attachment point of a base, the one or more fastener components being located within the notch such that the base at least partially resides within the attachment channel when the drawer housing is secured to the attachment point,
         a lock for securing a drawer within the interior volume,
         a processor for controllably locking and unlocking the lock, and
         a memory for storing one or more stored passcode values for unlocking the lock;
   the drawer that includes one or more compartments and is slidably movable with respect to the interior volume of the drawer housing between
      a closed position in which the compartments are inaccessible, and
      an open position in which the compartments are at least partially accessible;
   a drawer catch for releasing the drawer from the interior volume of the drawer housing when the drawer is in the open position; and
   an access pad mounted to an exterior surface of the drawer housing, the exterior surface being parallel to an access along which the drawer is slidably movable with respect to the interior volume of the drawer housing, where the access pad enables a user to enter a passcode, and
   where the processor is configured to unlock the lock when the passcode matches one of the one or more stored passcode values in the memory.

9. The drawer assembly of claim 8, wherein the base is part of a mobile cart structure or a wall.

10. The drawer assembly of claim 8, wherein the memory further comprises:
    a time threshold for how long the drawer is able to remain in an unlocked state,
    where the lock is configured to lock if the time threshold is reached.

11. The drawer assembly of claim 8, further comprising:
    one or more covers,
    wherein each cover is associated with at least one of the compartments, and
    wherein each cover is openable to provide access to the corresponding at least one compartment when the drawer is in the open position.

12. The drawer assembly of claim 11, wherein each cover is translucent or clear, which enables the user to determine if there are contents within each compartment.

13. The drawer assembly of claim 11, further comprising:
a data port that is connected to the processor and capable of interfacing with an external computer.

14. The drawer assembly of claim 13, wherein the memory includes instructions, which, when executed by the processor, cause the processor to:
establish a communication channel between the drawer assembly and the external computer via the data port;
receive information from the external computer at the data port; and
store at least some of the information in the memory.

15. The drawer assembly of claim 14, wherein the information includes acceptable passcode values for unlocking the drawer housing.

16. The drawer assembly of claim 13, wherein the memory includes instructions, which, when executed by the processor, cause the processor to:
establish a communication channel between the drawer assembly and the external computer via the data port; and
transfer information from the drawer assembly to the external computer through the data port.

17. The drawer assembly of claim 16, wherein the information includes time stamps corresponding to openings or closings of the drawer, entered passcode values, or both.

18. The drawer assembly of claim 11, wherein the access pad comprises any of a keypad, a card reader, a fingerprint scanner, a retina scanner, and a facial recognition system.

19. The drawer assembly of claim 11, wherein the drawer housing includes a lower surface and an upper surface that are interlock-able and stackably mountable upon other drawer housings.

20. A drawer assembly comprising:
a drawer housing defined by an upper surface and opposite sides extending downwardly from the upper surface, the drawer housing having
an opening that extends inward from a front end of the drawer housing to define an interior volume, and
a notch along a back end of the drawer housing to define an attachment channel;
a drawer that includes one or more compartments and is slidably movable with respect to the interior volume of the drawer housing between
a closed position in which the compartments are inaccessible, and
an open position in which the compartments are at least partially accessible;
an access pad mounted to one of the opposite sides of the drawer housing;
a lock for selectably locking and unlocking the drawer in response to entry of a passcode on the access pad; and
a fastener component for affixing the drawer housing to a base, the fastener component being located within the notch such that the base at least partially resides within the attachment channel when the drawer housing is affixed to the base.

* * * * *